(12) United States Patent
Shirota et al.

(10) Patent No.: US 7,160,634 B2
(45) Date of Patent: Jan. 9, 2007

(54) VINYL POLYMER AND ORGANIC ELECTROLUMINESCENT DEVICE

(75) Inventors: Yasuhiko Shirota, 3-5-7, Daikoku-cho, Toyonaka-shi, Osaka 561-0827 (JP); Yutaka Ohsedo, Sapporo (JP); Kazuyuki Moriwaki, Minoo (JP); Kenji Okumoto, Toyonaka (JP)

(73) Assignees: Yasuhiko Shirota, Toyonaka (JP); Daicel Chemical Industries, Ltd., Sakai (JP)

( * ) Notice: Subject to any disclaimer, the term of this patent is extended or adjusted under 35 U.S.C. 154(b) by 0 days.

(21) Appl. No.: 11/249,421

(22) Filed: Oct. 14, 2005

(65) Prior Publication Data

US 2006/0049750 A1   Mar. 9, 2006

Related U.S. Application Data

(62) Division of application No. 10/823,597, filed on Apr. 14, 2004, now Pat. No. 7,038,086, which is a division of application No. 10/237,951, filed on Sep. 10, 2002, now Pat. No. 6,784,318.

(30) Foreign Application Priority Data

Feb. 25, 2002   (JP)   ............................... 2002-47990

(51) Int. Cl.
- *H01J 1/62* (2006.01)
- *H01J 63/04* (2006.01)
- *H01L 29/08* (2006.01)
- *H01L 35/24* (2006.01)
- *H01L 51/00* (2006.01)
- *C08F 16/00* (2006.01)
- *C08F 14/00* (2006.01)

(52) U.S. Cl. ..................... 428/690; 313/504; 257/40; 526/310

(58) Field of Classification Search ..................... None
See application file for complete search history.

(56) References Cited

OTHER PUBLICATIONS

Y. Shirota et al., *Synthetic Metals*, vol. 41-43 (1991) pp. 3031-3036.
Kazunari Nawa et al., *Macromolecules*, vol. 28 (1995) pp. 723-729.
Yutaka Ohsedo et al., *Synthetic Metals*, vol. 81 (1996) pp. 157-162.
Ichiro Imae et al., *Macromolecules*, vol. 30 (1997) pp. 380-386.
Yutaka Ohsedo et al., *Synthetic Metals*, vol. 102 (1999) pp. 969-970.
Yutaka Ohsedo et al., *Electrochimica Acta*, vol. 45 (2000) pp. 1543-1547.
*Polymer Preprints*, Japan, vol. 50, No. 13 (2001) pp. 3385-3386 (with English translation).
Toshihide Yamamoto et al., *Tetrahedron Letters*, vol. 39 (1998) pp. 2367-2370.
Norio Miyaura et al., *Chem. Rev.*, vol. 95 (1995) pp. 2457-2483.

*Primary Examiner*—Brian Davis
(74) *Attorney, Agent, or Firm*—Birch, Stewart, Kolasch & Birch, LLP

(57) ABSTRACT

An organic electroluminescent device having an organic layer between a pair of electrodes. The organic layer (in particular, a hole-transporting layer) has a polymer of a vinyl compound represented by the following formula (1):

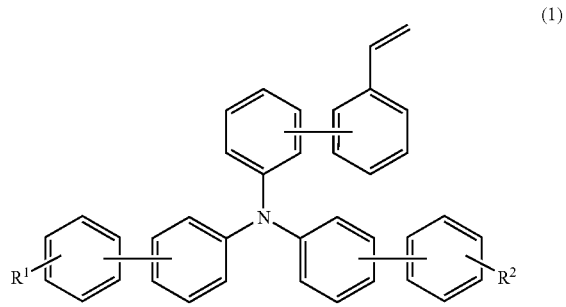

wherein $R^1$ and $R^2$ are the same or different, each representing a hydrogen atom, a halogen atom, an alkyl group or an alkoxy group. The glass transition temperature of the polymer is about 200 to 250° C., and the polymer has high heat-resistance. Thus, the use of the polymer improves heat resistance of an organic EL device.

5 Claims, 10 Drawing Sheets

VINYL POLYMER AND ORGANIC ELECTROLUMINESCENT DEVICE

CROSS-REFERENCE TO RELATED APPLICATIONS

This application is a Rule 53(b) divisional of U.S. application Ser. No. 10/823,597 filed Apr. 14, 2004, now U.S. Pat. No. 7,038,086, which is a Rule 53(b) divisional of U.S. application Ser. No. 10/237,951 filed on Sep. 10, 2002, now U.S. Pat. No. 6,784,318, which claims priority on Japanese Application No. 47990/2002 filed on Feb. 25, 2002. The entire contents of each of these applications is incorporated herein by reference.

FIELD OF THE INVENTION

The present invention relates to a vinyl polymer useful for forming an organic electroluminescent device excellent in heat resistance, a vinyl compound useful as a raw material of the vinyl polymer, and an organic electroluminescent device using the vinyl polymer.

BACKGROUND OF THE INVENTION

An organic electroluminescent device (hereinafter, occasionally referred as "an organic EL device") has been utilized in a display apparatus. In addition to properties such as high luminance (brightness), high light emission, full-colored display and durability, the organic EL device requires heat resistance (thermostability) because the device generates a large amount of heat when driving. In particular, when the organic EL device is used for interior lighting application and the like, it is predicted that a large amount of Joule heat is generated. Moreover, in the application such as an in-vehicle display, heat resistance is an important element because the surroundings may be exposed to high temperature. In this way, according to expansion of application of an organic EL device, it is practically important to improve heat resistance of an organic EL device.

An organic thin layer used for an organic EL device is usually an amorphous glass state from the viewpoint of mold-processability. Moreover, in order to make a device having high heat resistance, it is necessary to use an organic material having a high glass transition temperature for forming a thin layer.

Regarding a material for an organic EL device, before now, some kinds of materials forming an amorphous glass have been reported. However, inmost of these amorphous materials, a glass transition temperature (Tg) thereof is low and not more than or about 150° C. For example, as a hole-transporting material, compounds represented by the formulae (2a) to (2f) described below and having Tg of 75 to 151° C. have been proposed. As an electron-transporting material, compounds represented by the formulae (3a) to (3c) described below and having Tg of 107 to 136° C. have been proposed. Moreover, as a light emissive material, compounds represented by the formulae (4a) to (4c) described below and having Tg of 84 to 132° C. have been proposed. Incidentally, the inventors of the present invention found the compounds (2a) to (2f), (3a) to (3c) and (4a) to (4c).

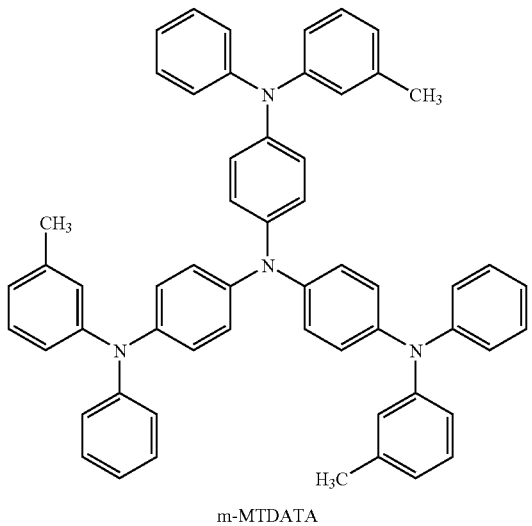

m-MTDATA
Tg = 75° C.
Chem. Lett., 1989, 1145.
Appl. Phys. Lett., 65, 807 (1994).

(2a)

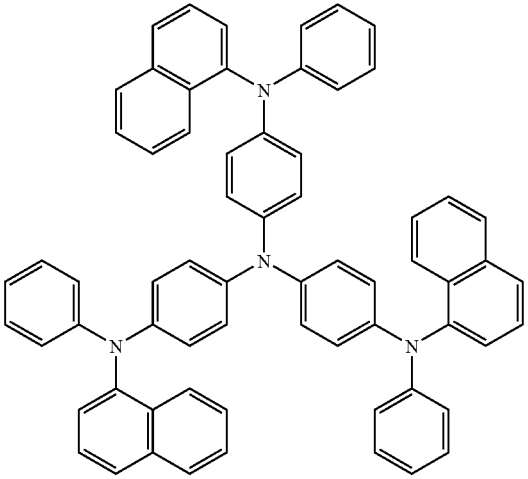

1-TNATA
Tg = 113° C.
J. Lumin., 72–74, 985 (1997).

(2b)

-continued
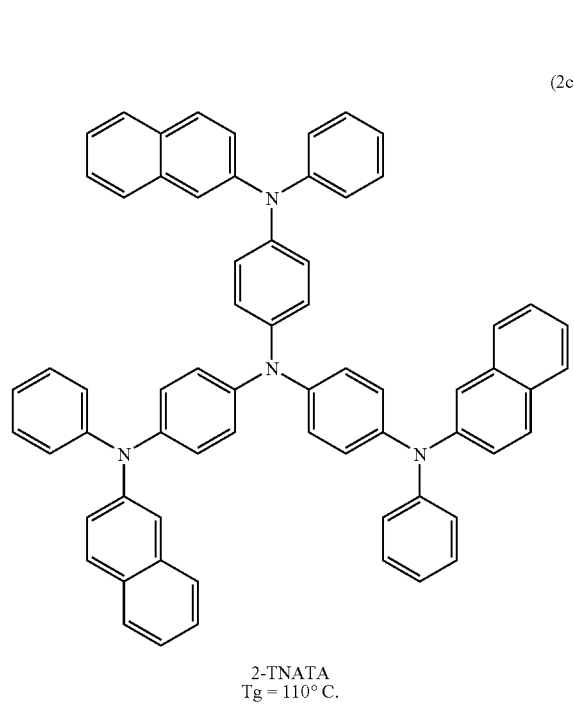
2-TNATA
Tg = 110° C.
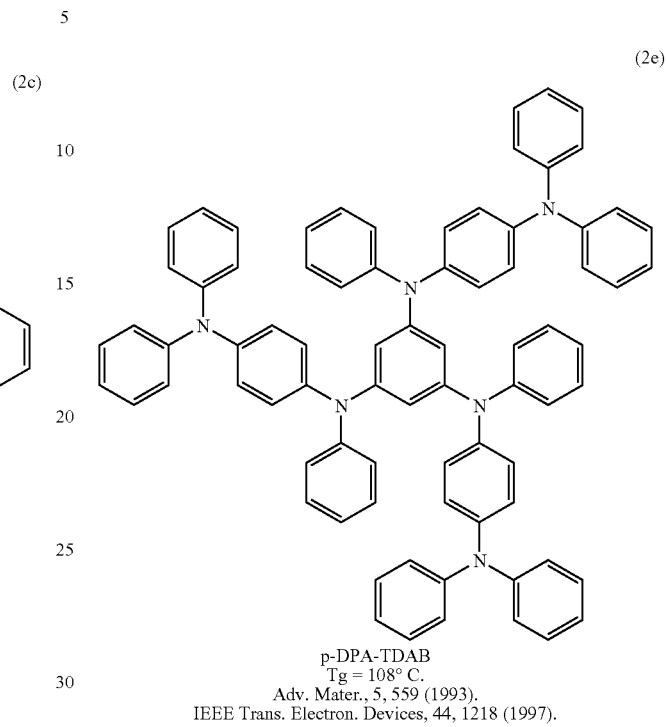
p-DPA-TDAB
Tg = 108° C.
Adv. Mater., 5, 559 (1993).
IEEE Trans. Electron. Devices, 44, 1218 (1997).
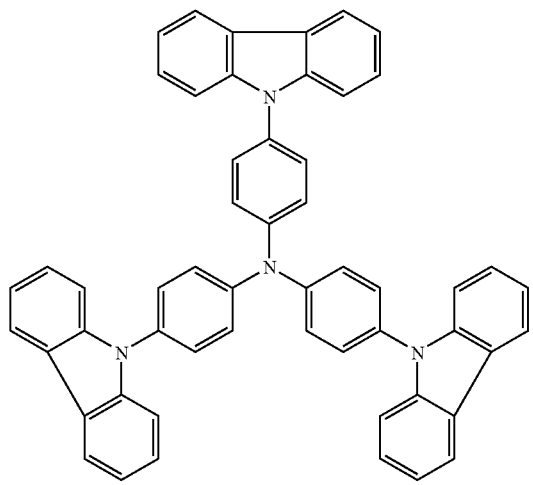
TCTA
Tg = 151° C.
Adv. Mater., 6, 677 (1994).
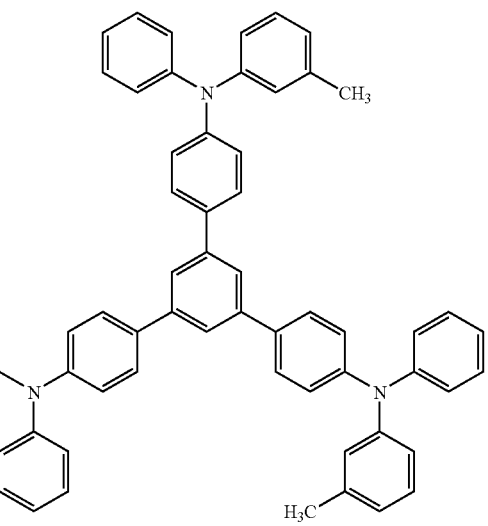
m-MTDAPB
Tg = 105° C.
J. Mater. Chem., 3, 319 (1993).
Mol. Cryst. Liq. Cryst., 280, 331 (1996).

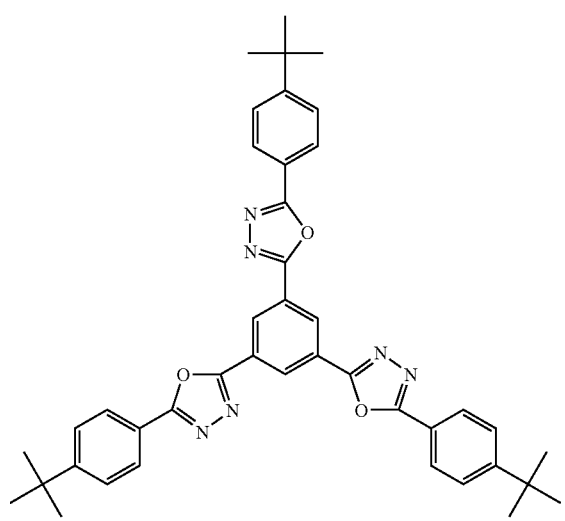
TBOB
Tg = 136° C.
J. Lumin., 72–74, 985 (1997).
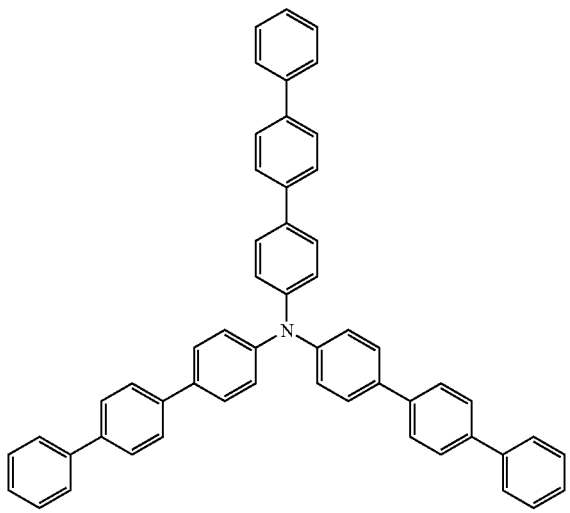
p-TTA
Tg = 132° C.
Synth. Met., 91, 243 (1997).
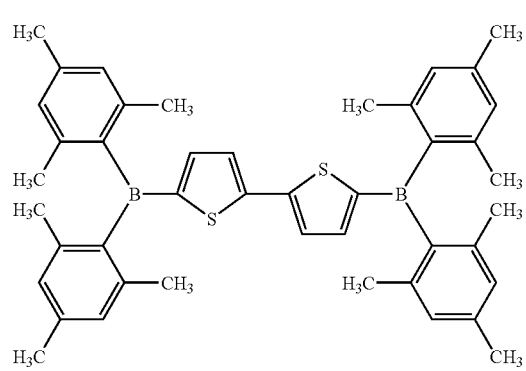
BMB-2T
Tg = 107° C.
J. Am. Chem. Soc., 120, 9714 (1999).
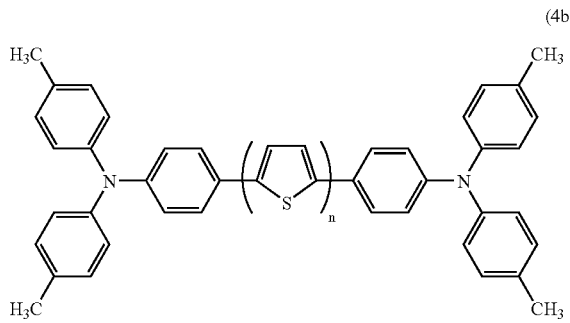
BMA-nT(n = 1–4)
Tg = 86–98° C.
Appl. Phys. Lett., 70, 699 (1997).
Adv. Mater., 9, 720 (1997).
J. Mater. Chem., 9, 2177 (1999).
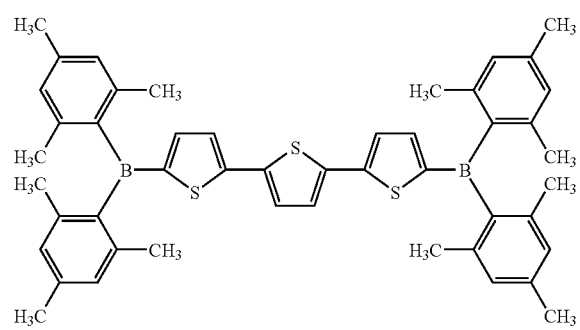
BMB-3T
Tg = 115° C.
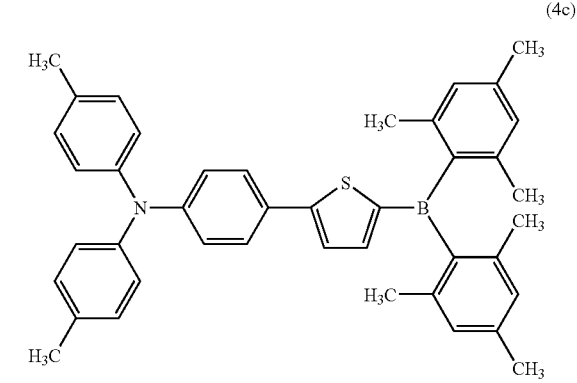
BMB-3T
Tg = 115° C.
J. Am. Chem. Soc., 122, 11021 (2000).

Since these materials have low glass transition temperatures, it is difficult to improve heat resistance of organic EL devices obtained from these materials. Moreover, mold-processability is insufficient in these materials.

As a material for a polymeric organic EL device, there have been known a main chain-type polymer having a π-electron system in a main chain thereof, or a side chain-type polymer having a π-electron system in a side chain thereof. These materials are excellent in mold-processability. The main chain-type polymer, for example, includes materials represented by the following formulae.

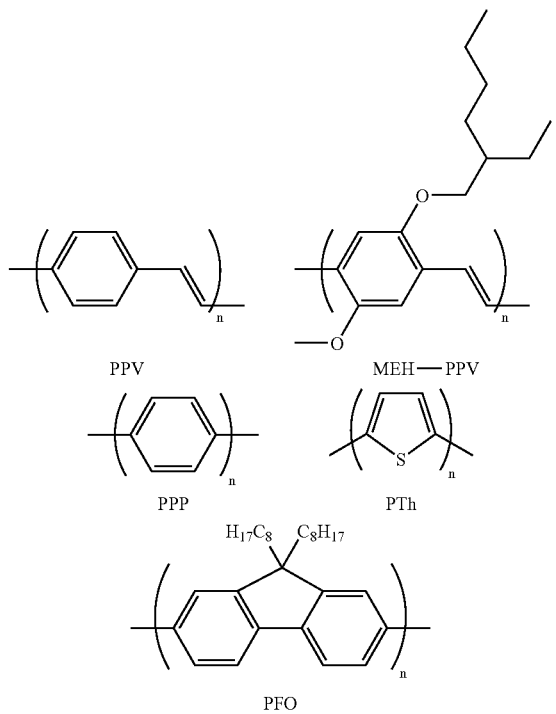

On the other hand, the side chain-type polymer has diversity of choices in a π-electron system chromophore constituting a side chain, and has superior chemical stability. Further, since an unconjugated-system structure in the side chain-type polymer is easily made in a main chain thereof, it is easy to impart mold-processability to the polymer. Moreover, the polymer has advantages such as excellent photoconductivity, and constant standard oxidation-reduction potential independent of doping rate. As such a side chain-type polymer, the inventors of the present invention have reported polymers comprising, as a side chain group having a π-electron system, carbazole, ferrocene, triphenylamine, pyrene, perylene, an oligothiophene and the like, and have clarified that these polymers are applicable to a cathode material for a secondary cell, a p-mode semiconductor material for a photoelectric transfer device, an electrochromic material and other materials [Synth. Met., 41–43, 3031 (1991), and literatures described therein, for example, Macromolecules, 28, 723 (1995); Synth. Met., 81, 157 (1996); Macromolecules, 30, 380 (1997); Synth. Met., 102, 969 (1999); and Electrochim. Acta, 45, 1543 (2000)]. However, even in the polymer materials described in these literatures, it is difficult to improve heat resistance due to their low glass transition temperature.

In this way, a polymeric material having a high glass transition temperature is required in order to improve heat resistance and mold-processability of an organic EL device.

SUMMARY OF THE INVENTION

It is, therefore, an object of the present invention to provide a vinyl polymer excellent in heat resistance and mold-processability and useful as a material for an organic EL device, and a vinyl compound useful for obtaining the vinyl polymer.

It is another object of the invention to provide an organic EL device having superior heat resistance.

The inventors of the present invention made intensive studies to achieve the above objects and finally found that a vinyl polymer, which is obtainable from a novel vinyl compound having a tris(biphenylyl)amine backbone as a side chain group having a π-electron system, is useful as a hole-transporting material for an organic EL device and has high heat resistance. The present invention was accomplished based on the above finding.

That is, the vinyl compound of the present invention is represented by the following formula (1):

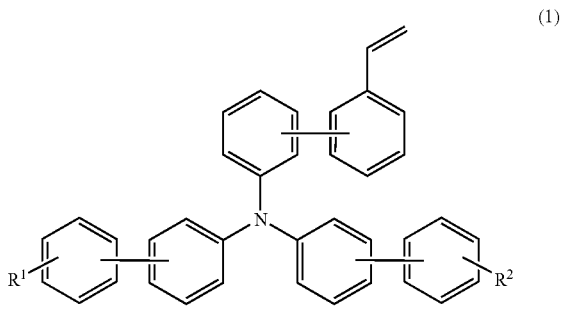

wherein $R^1$ and $R^2$ are the same or different, each representing a hydrogen atom, a halogen atom, an alkyl group or an alkoxy group.

In the above formula, the $R^1$ and $R^2$ may be a hydrogen atom, a halogen atom, a linear or branched $C_{1-6}$alkyl group or a $C_{1-6}$alkoxy group. Preferably, the $R^1$ and $R^2$ may be a hydrogen atom, a $C_{1-4}$alkyl group or a $C_{1-4}$alkoxy group.

The vinyl compound may be represented by the following formula:

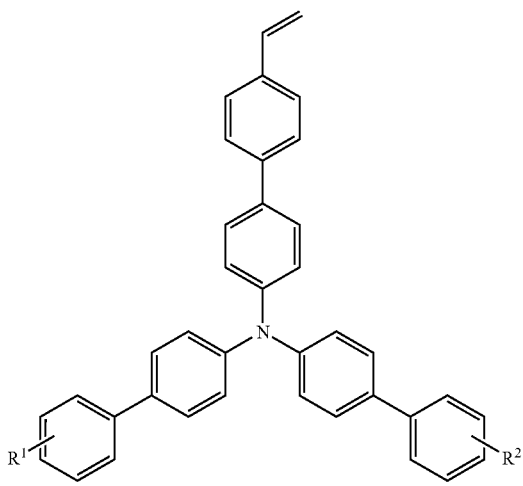

wherein $R^1$ and $R^2$ have the same meanings defined above.

The vinyl polymer of the present invention has a unit represented by the following formula (2):

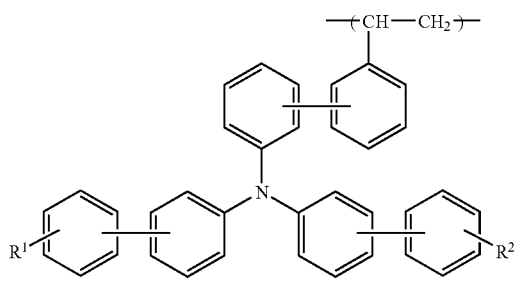

(2)

wherein R$^1$ and R$^2$ are the same or different, each representing a hydrogen atom, a halogen atom, an alkyl group or an alkoxy group.

The vinyl polymer may be a homopolymer of the vinyl compound, or a copolymer of the vinyl compound and a copolymerizable monomer. The glass transition temperature of the vinyl polymer may be about 200 to 250° C. The number-average molecular weight of the vinyl polymer may be 5,000 to 500,000.

The present invention also includes an organic electroluminescent device comprising an organic layer between a pair of electrodes, and the organic layer comprises at least one layer containing the vinyl polymer. The organic layer may comprise a hole-transporting layer containing the vinyl polymer. For example, the organic layer comprises (1) a hole-transporting layer containing the vinyl polymer, a light-emitting layer and an electron-transporting layer, or (2) a hole-transporting layer containing the vinyl polymer and a light-emissive electron-transporting layer. The organic layer may further comprise an anode buffer layer.

DETAILED DESCRIPTION OF THE INVENTION

[Vinyl Compound]

Figure 1:
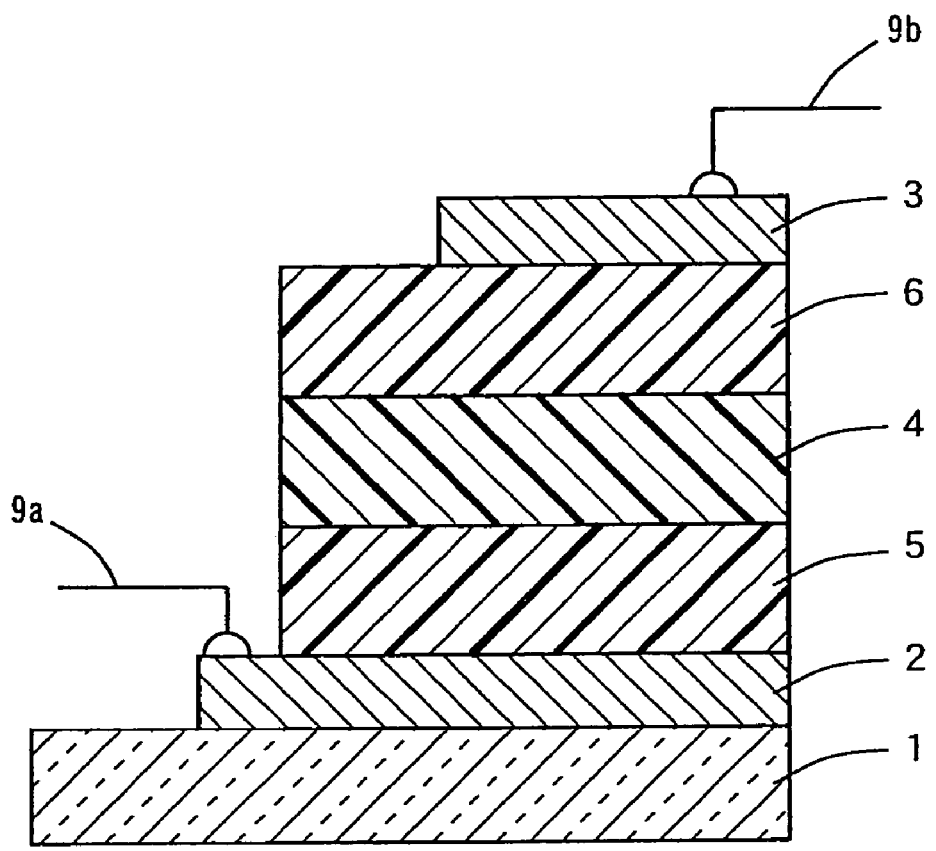
FIG. 1 is a schematic sectional view showing an embodiment of the organic EL device of the present invention.

A vinyl compound (vinyl monomer) represented by the above formula (1) is a novel compound. In the above formula (1), the halogen atom represented by R$^1$ and R$^2$ includes fluorine, chlorine, bromine, and iodine atoms. The alkyl group includes a linear or branched C$_{1-6}$alkyl group such as methyl, ethyl, n-propyl, sec-propyl, n-butyl, s-butyl, and t-butyl groups (preferably a linear or branched C$_{1-4}$alkyl group). The alkoxy group includes a C$_{1-6}$alkoxy group such as methoxy, ethoxy, propoxy, butoxy, and t-butoxy groups (preferably a C$_{1-4}$alkoxy group, and in particular a C$_{1-2}$alkoxy group).

The position to be substituted of the R$^1$ and R$^2$ is not particularly limited, and may be any of o-, m- and p-positions. The position is usually p-position. The position to be substituted of the vinyl group is not also particularly limited, and may be any of o-, m- and p-positions of a phenyl group. The position is usually m- or p-position.

In the above formula (1), a binding site of two benzene rings constituting a biphenylyl group is not particularly limited. The binding position of one benzene ring may be any of o-, m- and p-positions of the other benzene ring bonded to a nitrogen atom, and is usually p-position. That is, the preferred biphenylyl group is 4-phenylphenyl group.

The vinyl monomer can be produced, for example, by combining a production process of a triarylamine (e.g., Tetrahedron Lett., 39 (1998) 2367) and an aromatic coupling reaction (e.g., Chem. Rev., 95 (1995) 2457).

More specifically, a vinyl compound (1) having 4-phenylphenyl group as a biphenylyl group can, for example, be obtained according to the reaction scheme described below. That is, a bis(biphenylyl)halogenated phenylamine represented by the formula (1c) is formed by the reaction of aniline represented by the formula (1a) with a halogenated biphenyl compound represented by the formula (1b) and halogenation reaction, and thus obtained bis(biphenylyl) halogenated phenylamine (1c) is reacted with p-(dihydroxyboro)styrene represented by the formula (1f) to obtain the vinyl compound (1). Incidentally, p-(dihydroxyboro)styrene represented by the formula (1f) can be obtained by preparing, from a halostyrene (1d), a Grignard reagent (1e) corresponding to the halostyrene and reacting the Grignard reagent (1e) with boric acid.

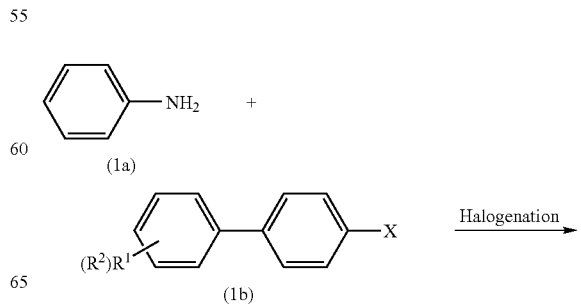

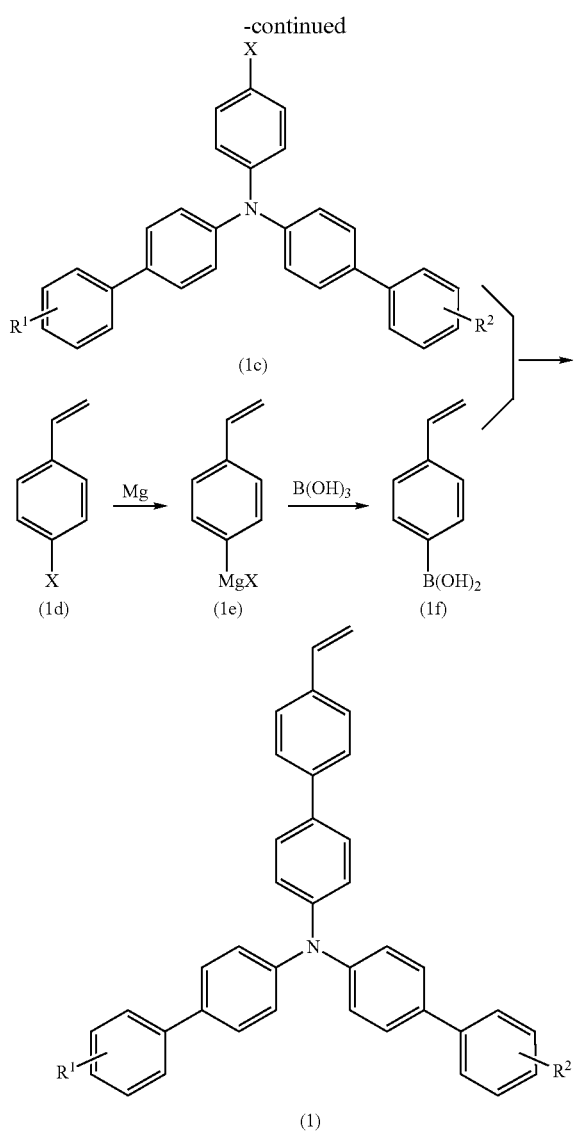

Wherein X represents a halogen atom, $R^1$ and $R^2$ have the same meanings as defined above.

The halogen atom represented by X includes fluorine, chlorine, bromine, and iodine atoms. Bromine and iodine atoms (in particular, bromine atom) are preferred.

The reaction of aniline (1a) with a halogenated biphenyl compound (1b) may be carried out in the presence of a base, if necessary with the use of a catalyst. The amount of the halogenated biphenyl compound (1b) is usually about 1.5 to 2.5 mol, and preferably about 1.8 to 2.2 mol relative to 1 mol of aniline (1a).

As the base, an inorganic base, for example, an alkali metal alkoxide may be used. The alkali metal alkoxide includes, for example, an alkali metal $C_{1-6}$alkoxide such as sodium methoxide, sodium ethoxide and sodium t-butoxide (in particular, a sodium $C_{1-4}$alkoxide). The ratio of the alkali metal alkoxide is about 0.5 to 10 mol, preferably about 1 to 5 mol, and more preferably about 2 to 3 mol relative to 1 mol of aniline.

The reaction may be carried out in the presence of a catalyst. As the catalyst, a palladium catalyst such as bis (dibenzalacetone)palladium [Pd(dba)$_2$] may be used. Incidentally, it is desirable that the palladium catalyst is used, for example, in combination with a phosphorus ligand (phosphorus atom-containing ligand) such as 1,1'-bis(diphenylphosphino)ferrocene (DPPF). The amount to be used of the palladium catalyst can be selected within the range of about 0.001 to 1 mol, and preferably about 0.001 to 0.5 mol relative to 1 mol of aniline. In the case where the palladium catalyst is used in combination with the phosphorus ligand, the ratio (molar ratio) of the palladium catalyst relative to the phosphorus ligand is about 1/10 to 5/1, preferably about 1/5 to 2/1, and more preferably about 1/3 to 1/1.

The reaction may be carried out in the presence of a solvent inert to the reaction, for example, an aliphatic hydrocarbon (e.g., hexane), an alicyclic hydrocarbon (e.g., cyclohexane), an aromatic hydrocarbon (e.g., benzene, toluene), an alcohol (e.g., methanol, ethanol, isopropyl alcohol, butanol), an ester (e.g., ethyl acetate, butyl acetate, isobutyl acetate), an ether (e.g., a chain ether such as diethyl ether, a cyclic ether such as dioxane and tetrahydrofuran), a nitrile (e.g., acetonitrile, benzonitrile), a sulfoxide (e.g., dimethyl sulfoxide). As the reaction solvent, the hydrocarbon, for example, the aromatic hydrocarbon such as toluene, is usually employed.

The compound represented by the formula (1c) can be produced by halogenating a biphenylamine compound the above-mentioned reaction of the aniline (1a) with the halogenated biphenyl compound (1b). The biphenylamine compound obtained by the reaction of the aniline (1a) with the halogenated biphenyl compound (1b) may be separated and purified from the reaction mixture and subjected to a halogenation reaction, or may be subjected to a halogenation reaction without separation and purification. The halogenation reaction can be carried out by a conventional manner, and for example, can be carried out with the use of an N-halodicarboxylic imide [in particular, N-bromosuccinic imide (NBS)]. The amount to be used of the N-halodicarboxylic imide is for example about 0.5 to 5 mol, preferably about 0.7 to 2 mol, and in particular about 1 to 2 mol relative to 1 mol of the aniline (1a) or the biphenyl compound (1c). If necessary, the reaction may be carried out in the presence of a radical-generating agent (e.g., an azo compound such as azobisisobutyronitrile, an organic peroxide such as benzoyl peroxide). Further, the reaction may be carried out in the presence of a solvent. Such a solvent includes, in addition to the above-exemplified solvent, an amide (e.g., formamide, acetamide, dimethylformamide (DMF), and dimethylacetamide), a halogenated hydrocarbon (e.g., chloroform), and the like. The preferred solvent is the halogenated hydrocarbon.

In the reaction of the aniline (1a) with the halogenated biphenyl compound (1b) and the halogenation reaction, when a solvent is used, the reaction temperature can be selected within the range of 0° C. to reflux temperature and is for example about 50 to 120° C., preferably about 60to 100° C. The reactions can be conducted under ordinary pressure, reduced pressure, or applied pressure. Moreover, the reactions may be carried out in an atmosphere of an inert gas (e.g., nitrogen, argon, and helium).

If necessary, the bis(biphenylyl)halogenated phenylamine (1c) formed in the above-described reactions may be separated and purified by such a conventional means as filtration, condensation, distillation, extraction, crystallization, recrystallization, column chromatography, or a combination means thereof, and subjected to a reaction with p-(dihydroxyboro)styrene (1f).

The reaction of the formed bis(biphenylyl)halogenated phenylamine (1c) with p-(dihydroxyboro)styrene (1f) may be usually carried out in the presence of a base [e.g., an inorganic base such as an alkali metal hydroxide (such as sodium hydroxide and potassium hydroxide), an alkali metal carbonate (such as sodium carbonate, potassium carbonate, sodium hydrogen carbonate and potassium hydrogen carbonate); and an organic base]. If necessary, the reaction may be carried out in the presence of a catalyst. As the catalyst, there may be used a palladium catalyst such as palladium tetrakis (triphenylphosphine). The ratio of the base is about 0.5 to 3 mol, preferably about 0.8 to 2 mol, and more preferably about 1 to 1.5 mol relative to 1 mol of the bis(biphenylyl)halogenated phenylamine. The ratio of the catalyst is about 0.0001 to 0.5 mol, and preferably about 0.001 to 0.1 mol relative to 1 mol of the bis(biphenylyl) halogenated phenylamine.

The reaction may be carried out in the presence of a solvent, for example, the above-exemplified reaction solvent. The reaction temperature can be selected within the range of the above-mentioned reaction temperature. The reaction can be effected under ordinary pressure, reduced pressure, or applied pressure. The reaction may be carried out in an atmosphere of an inert gas (e.g., nitrogen, argon, and helium).

Moreover, p-(dihydroxyboro) styrene represented by the formula (1f) can be obtained by preparing, from a halostyrene (1d), a Grignard reagent (1e) corresponding to the halostyrene (1d), and reacting the Grignard reagent (1e) with boric acid. For example, p-(dihydroxyboro)styrene (1f) can be obtained by allowing the p-halostyrene (e.g., p-bromostyrene, p-iodostyrene) to react with a metal magnesium in an ether (e.g., a non-cyclic ether such as diethyl ether, a cyclic ether such as tetrahydrofuran) to form the Grignard reagent (p-vinylphenylmagnesium halide) (1e), and treating the Grignard reagent with orthoboric acid and water sequentially. As the ether of the reaction solvent, it is preferred to use one substantially free from water or an alcohol.

In the reaction of the compound (1d) with magnesium, the ratio of the metal magnesium may be an excessive amount (molar amount) relative to the p-halostyrene and, for example, can be selected within the range of about 1 to 10 mol relative to 1 mol of the p-halostyrene. The reaction temperature for obtaining the Grignard reagent (1e) is not particularly limited, and for example about −20° C. to 50° C., preferably about −10° C. to 30° C.

The ratio of the orthoboric acid relative to the Grignard reagent (1e) is about 1 to 10 mol relative to 1 mol of the Grignard reagent (1e). The ratio of water may be an excessive amount (molar amount) relative to the Grignard reagent (1e) and, for example, can be selected within the range of about 0.5 to 50 mol, relative to 1 mol of the Grignard reagent (1e).

The reaction may be effected under reduced pressure, or applied pressure. The reaction may be usually effected under ordinary pressure. Moreover, the reaction may be carried out in an atmosphere of an inert gas (e.g., nitrogen, argon, and helium).

After completion of the reaction, the formed vinyl compound (1) can be easily separated and purified by such a conventional means as filtration, condensation, distillation, extraction, crystallization, recrystallization, column chromatography, or a combination means thereof.

The vinyl compound represented by the formula (1) includes, for example, 4-[bis(biphenyl-4-yl)amino]-4'-vinylbiphenyl; a 4-[bis(4-halobiphenyl-4-yl)amino]-4'-vinylbiphenyl (e.g., 4-[bis(4-chlorobiphenyl-4-yl)amino]-4'-vinylbiphenyl, 4-[bis(4-bromobiphenyl-4-yl)amino]-4'-vinylbiphenyl, 4-[bis(4-fluorobiphenyl-4-yl)amino]-4'-vinylbiphenyl); a 4-[bis(4-$C_{1-6}$alkylbiphenyl-4-yl)amino]-4'-vinylbiphenyl (e.g., 4-[bis(4-methylbiphenyl-4-yl) amino]-4'-vinylbiphenyl, 4-[bis(4-ethylbiphenyl-4-yl) amino]-4'-vinylbiphenyl, 4-[bis(4-isopropylbiphenyl-4-yl) amino]-4'-vinylbiphenyl, 4-[bis(4-t-butylbiphenyl-4-yl) amino]-4'-vinylbiphenyl); a 4-[bis(4-$C_{1-6}$alkoxybiphenyl-4-yl)amino]-4'-vinylbiphenyl (e.g., 4-[bis(4-methoxybiphenyl-4-yl)amino]-4'-vinylbiphenyl, 4-[bis(4-ethoxybiphenyl-4-yl)amino]-4'-vinylbiphenyl, 4-[bis(4-t-butoxybiphenyl-4-yl)amino]-4'-vinylbiphenyl); and others, and includes compounds, which are corresponding to the above-exemplified compounds and are different from the above-exemplified compounds in a position having a substituent, for example 4-[bis(biphenyl-4-yl)amino]-4'-vinylbiphenyl; a 4-[bis(3-halobiphenyl-4-yl)amino]-4'-vinylbiphenyl; a 4-[bis(3-$C_{1-6}$alkylbiphenyl-4-yl)amino]-4'-vinylbiphenyl; and a 4-[bis(3-$C_{1-6}$alkoxybiphenyl-4-yl) amino]-4'-vinylbiphenyl.

Thus obtained vinyl compound (1) is useful for producing or forming a polymer having an excellent hole-transporting ability.

[Vinyl Polymer]

The vinyl polymer of the present invention has a unit represented by the formula (2), and can be obtained by allowing at least the vinyl compound (1) to polymerize in the presence of a radical initiator. The vinyl compound (1) may be used singly or in combination. That is, the vinyl polymer having the unit (2) (hereinafter sometimes refers as the vinyl polymer (2)) may be a homo- or copolymer of the vinyl compound (1), or may be a copolymer of the vinyl compound (1) and a copolymerizable monomer. Such a vinyl polymer has a side chain of a π-electron system, and has an excellent hole-transporting function, additionally high mold-processability and high chemical-stability. In particular, on account of having extremely high glass transition temperature, the vinyl polymer realizes great improvement in heat resistance.

The copolymerizable monomer includes an aromatic vinyl monomer (e.g., styrene or a substituted compound thereof such as styrene, vinyltoluene and α-methylstyrene), a vinyl cyanide-series monomer (e.g., acrylonitrile), an unsaturated polycarboxylic acid or an acid anhydride thereof (e.g., maleic acid, itaconic acid, citraconic acid, or an acid anhydride thereof), an imide-series monomer [e.g., maleimide, an N-alkylmaleimide (e.g., an N—$C_{1-4}$alkylmaleimide), an N-cycloalkylmaleimide (e.g., N-cyclohexylmaleimide), an N-arylmaleimide (e.g., N-phenylmaleimide)], an acrylic monomer [e.g., (meth)acrylic acid, a $C_{1-20}$alkyl ester of (meth)acrylic acid such as methyl(meth)acrylate], a vinylcarbazole (e.g., N-vinylcarbazole, dibromo-N-vinylcarbazole, N-vinylcarbazolylethyl vinyl ether), a vinylferrocene, an N,N-diarylaminoaryl$C_{2-4}$alkyl(meth)acrylate (e.g., N,N-diphenylaminophenylethyl(meth)acrylate), a condensed cyclic vinyl compound (e.g., vinylpyrene, vinylperylene, perylenylethyl(meth)acrylate) and others. The copolymerizable monomer may be used singly or in combination. The amount to be used of the copolymerizable monomer relative to the amount of the total monomer can be usually selected within the range of about 0.1 to 30% by weight, preferably about 1 to 20% by weight, and more preferably about 1 to 10% by weight.

The radical initiator includes a conventional radical initiator, for example, an azo-series compound [e.g., azobisisobutyronitrile (AIBN), dimethylazoisobutylate, benzene diazonium chloride], and a peroxide (e.g., benzoyl peroxide, di-t-butyl peroxide, t-butyl perbenzoate, hydrogen peroxide). The ratio of the radical initiator is not particularly limited, and about 0.01 to 20 parts by weight, preferably about 0.1 to 10 parts by weight, and more preferably about 1 to 5 parts by weight relative to 100 parts by weight of the total amount of the vinyl monomer.

The polymerization can be carried out in a conventional method, for example, solution polymerization, suspension polymerization, and the solution polymerization is usually utilized. As a solvent for solution polymerization, a variety of solvents which dissolve (or can dissolve) a formed polymer can be employed, such as a hydrocarbon, an ester, a ketone, an ether and others. An aromatic hydrocarbon such as benzene and toluene is usually employed.

The polymerization temperature is not particularly limited, and can be selected within the wide range of about 0 to 200° C. In the solution polymerization, the polymerization temperature is usually not higher than reflux temperature of the solvent, for example, room temperature (about 20 to 30° C.) to 100° C., preferably about 50 to 100° C. The polymerization time is not particularly limited, and can be selected within the range of about 0.5 to 72 hours, and preferably about 5 to 48 hours. The polymerization is usually carried out in an atmosphere of an inert gas. As the inert gas, there may be exemplified nitrogen, helium, and argon gas.

The formed polymer can be separated and purified by such a conventional manner as precipitation method utilizing a solubilizing solvent and a poor solvent, or column chromatography.

The glass transition temperature of the vinyl polymer having the unit (2) is for example so high as about 160 to 280° C. (e.g., about 180 to 280° C.), preferably about 200 to 270° C., and more preferably about 210 to 250° C. Use of a vinyl polymer having such a high Tg as a material for an organic EL device realizes an organic EL device having extremely high heat resistance.

The weight-average molecular weight (Mw) of the vinyl polymer (2) (in terms of polystyrene) is about 5,000 to 500,000, preferably about 5,000 to 100,000, and more preferably about 10,000 to 50,000. The number-average molecular weight (Mn) is about 5,000 to 500,000, preferably about 5,000 to 100,000, and more preferably about 10,000 to 40,000. Moreover, the molecular weight distribution (Mw/Mn) of the vinyl polymer (2) is for example about 1 to 3, and preferably about 1 to 2 (in particular, about 1 to 1.7).

As concrete examples of such a vinyl polymer, for example, there may be illustrated a polymer comprising, as the unit (2), at least one unit selected from units represented by the following formulae:

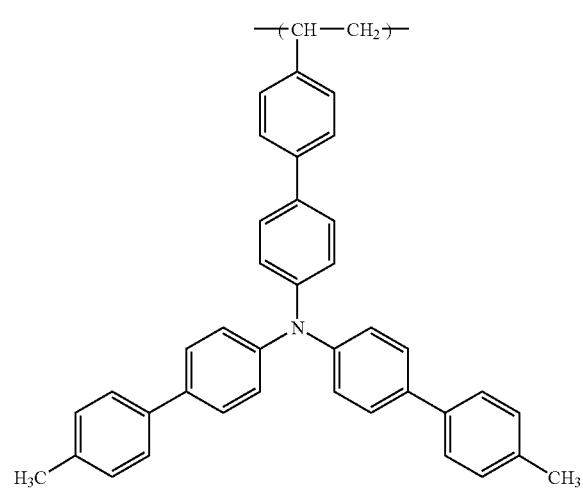

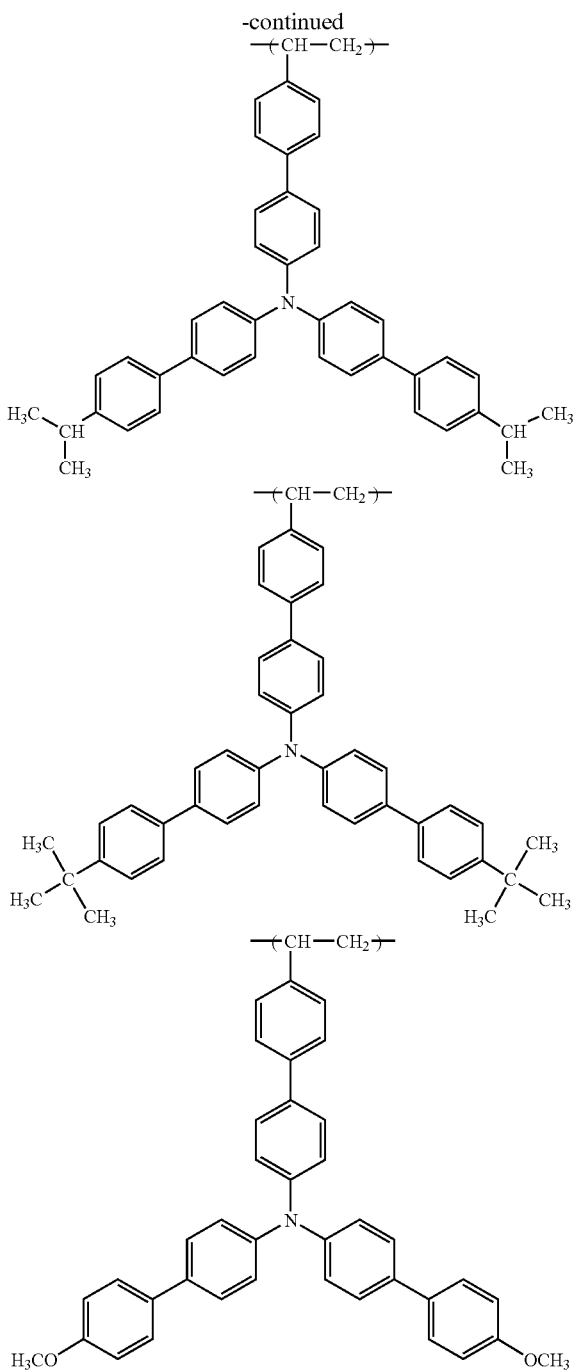

Such a vinyl polymer (2) is capable of easily forming a uniform and transparent amorphous glass by means of a variety of methods for forming a coating layer (for example, a variety of coating methods such as spin coating, casting).

[Organic EL Device]

The organic EL device of the present invention comprises a pair of electrodes and an organic layer interposed therebetween. The organic layer comprises at least a vinyl polymer having a unit represented by the above formula (2). For example, the organic layer may comprise at least one layer containing the vinyl polymer. In a typical example, the organic layer may comprise a hole-transporting layer, a light-emitting (luminiferous) layer and a electron-transporting layer, or may comprise a hole-transporting layer and a light-emissive (luminiferous) electron-transporting layer.

A layer comprising the vinyl polymer usually has a hole (or positive hole)-transporting function, and constitutes a hole-transporting layer. Moreover, the vinyl polymer (2) can be also used as a host layer of a light-emissive (luminiferous) dopant dye (coloring matter or pigment). The dopant dye is not particularly limited, and includes a light-emissive (luminiferous) compound described later: for example, a condensed polycyclic hydrocarbon, which may have a substituent (e.g., a halogen atom, a $C_{1-4}$alkyl group, a $C_{1-4}$alkoxy group, a carbonyl group, an amino group, a dialkylamino group, a cyano group), such as rubrene, pyrene, chrysene, perylene and coronene; and a condensed heterocyclic compound, which may have a substituent (e.g., a halogen atom, a $C_{1-4}$alkyl group, a $C_{1-4}$alkoxy group, a carbonyl group, an amino group, a dialkylamino group, a cyano group), such as a quinacridone (e.g., dimethylquinacridone, diethylquinacridone) and coumarin-6.

FIG. 1 is a schematic sectional view showing an embodiment of the organic EL device of the present invention. In the embodiment, the organic EL device has a laminated structure (lamination) which comprises a transparent electrode (anode) 2 formed on a transparent substrate (e.g., a glass substrate) 1, a hole-transporting layer 5 formed on the transparent electrode 2 and containing the vinyl polymer, a light-emitting layer 4 formed on the hole-transporting layer 5, an electron-transporting layer 6 formed on the light-emitting layer 4, and a cathode 3 formed on the electron-transporting layer 6. The anode 2 and the cathode 3 are connected with lead wires 9a and 9b, respectively.

Figure 2:
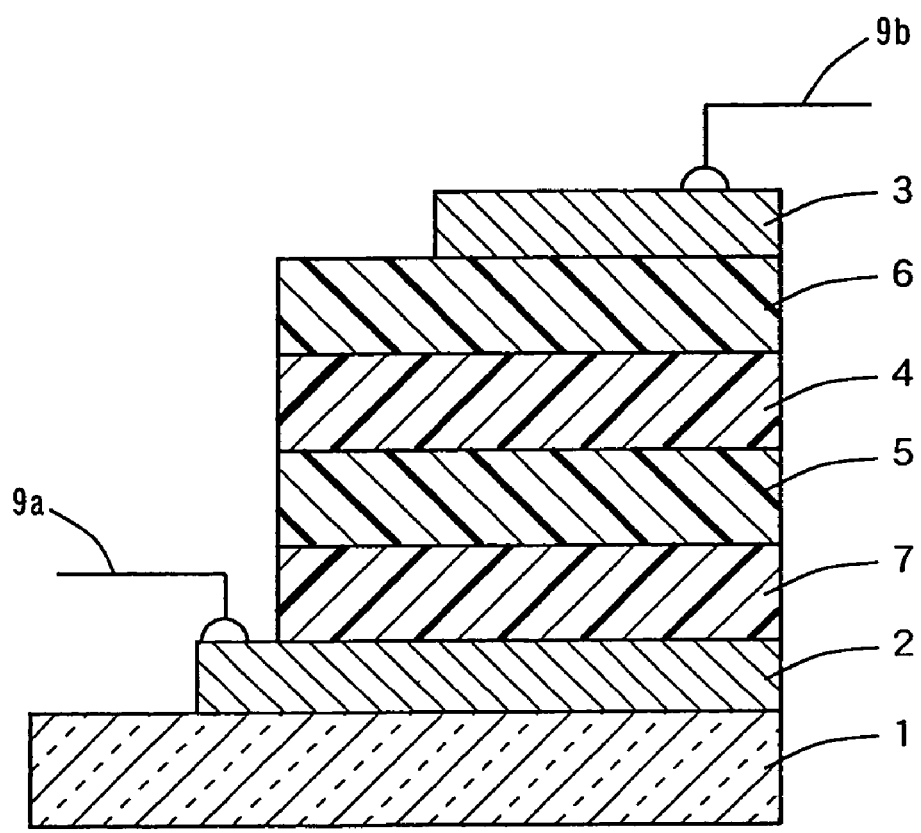
FIG. 2 is a schematic sectional view showing an another embodiment of the organic EL device of the present invention.
Figure 3:
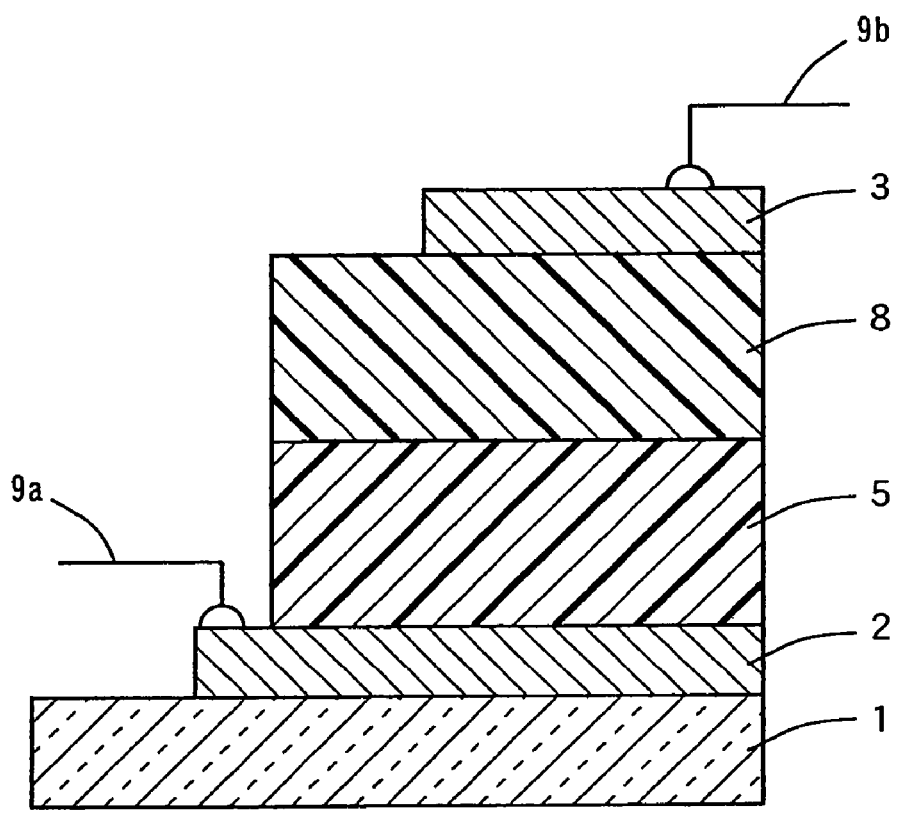
FIG. 3 is a schematic sectional view showing a still another embodiment of the organic EL device of the present invention.

FIG. 2 is a schematic sectional view showing another embodiment of the organic EL device of the present invention. In the organic EL device shown in FIG. 2, an anode buffer layer (hole-injecting layer) 7 is further interposed between the transparent electrode 2 and the hole-transporting layer 5 in the device shown in FIG. 1. Further, FIG. 3, illustrating a still another embodiment of the organic EL device of the present invention, shows an organic EL device having a laminated structure (lamination) which comprises a hole-transporting layer 5 formed on a transparent electrode 2 and containing the vinyl polymer, a light-emissive electron-transporting layer 8 formed on the hole-transporting layer 5, and a cathode 3 formed on the light-emissive electron-transporting layer 8. Furthermore, in the organic EL device shown in FIG. 4, an anode buffer layer (hole-injecting layer) 7 is further interposed between the transparent electrode (anode) 2 and the hole-transporting layer 5 in the device shown in FIG. 3.

Incidentally, in order to impart a light-emitting function to the hole-transporting layer comprising the vinyl polymer having the unit (2), an organic compound or polymer having a light-emitting function may be added to the hole-transporting layer, or a light-emitting layer composed of an organic compound or polymer having a light-emitting function may be laminated on the hole-transporting layer. Moreover, the electron-transporting layer may comprise an organic compound or polymer having an electron-transporting function, or may be formed as a light-emissive electron-transporting layer having a light-emitting function in combination with an electron-transporting function.

The hole-transporting layer may comprise a vinyl polymer having the unit (2) singly or in combination with an organic compound having a hole-transporting function (a hole-transporting compound). As the hole-transporting compound, there may be exemplified an aromatic tertiary amine such as N,N'-diphenyl-N,N'-bis(3-methylphenyl)-1,1'-biphenyl-4,4'-diamine (TPD), N,N'-diphenyl-N,N'-bis(1-naphthyl)-1,1'-biphenyl-4,4'-diamine (NPD), 1,1-bis[(di-4-tolylamino)phenyl]cyclohexane, N,N,N'N'-tetra(3-methylphenyl)-1,3-diaminobenzene (PDA), 4,4',4"-tris(3-methylphenylphenylamino)triphenylamine (m-MTDATA), 4,4',4"-tris(1-naphthylphenylamino)triphenylamine (1-TNATA), 4,4',4"-tris(2-naphthylphenylamino)triphenylamine (2-TNATA), 4,4',4"-tri(N-carbazolyl)triphenylamine (TCTA), 1,3,5-tris[4-(3-methylphenylphenylamino)phenyl]benzene (m-MTDAPB) and triphenylamine; and a phthalocyanine. The hole-transporting compound(s) can be used either singly or in combination.

A compound emitting a light by being excited by an electron and/or a hole (positive hole) may be used as the organic compound or polymer having a light-emitting function (a light-emissive compound). The light-emissive compound (emission center-forming compound) includes a heterocyclic compound (containing at least one hetero atom selected from oxygen, nitrogen and sulfur atoms) [e.g., a bis($C_{1-6}$alkyl-benzoxazolyl)thiophene such as 2,5-bis(5-tert-butyl-2-benzoxazolyl)thiophene; BMA-nT represented by the formula (4b) (n=1 to 4); PhAMB-1T represented by the formula (4c) ; nile red; a coumarin such as coumarin 6 and coumarin 7; a 4-(dicyano$C_{1-4}$alkylene)-2-$C_{1-4}$alkyl-6-(p-di$C_{1-4}$alkylaminostyryl)-4H-pyran such as 4-(dicyanomethylene)-2-methyl-6-(p-dimethylaminostyryl)-4H-pyran; and a quinacridone such as dimethylquinacridone and diethylquinacridone], which may have a substituent (such as a halogen atom, a $C_{1-4}$alkyl group, a $C_{1-4}$alkoxy group, a carbonyl group, an amino group, a dialkylamino group and a cyano group) ; a condensed polycyclic hydrocarbon such as rubrene, pyrene, chrysene, perylene and coronene; a tetra$C_{6-12}$aryl-1,3-butadiene such as 1,1,4,4-tetraphenyl-1,3-butadiene (TPB); a bis(2-(4-$C_{1-4}$alkylphenyl)$C_{2-4}$alkynyl)benzene such as 1,4-bis(2-(4-ethylphenyl)ethynyl)benzene; a bis(2,2'-di$C_{6-12}$arylvinyl)biphenyl such as 4,4'-bis(2,2'-diphenylvinyl)biphenyl; and N,N,N-tris(terphenylamine)(p-TTA) represented by the formula (4a). The light-emissive compound(s) may be used singly or in combination.

Examples of the organic compound having an electron-transporting function include an oxadiazole derivative [for example, an oxadiazole derivative having a $C_{6-20}$aryl group which may have a substituent, such as 2-(4-biphenyl)-5-(4-tert-butylphenyl)-1,3,4-oxadiazole (PBD), 2,5-bis(1-naphtyl)-1,3,4-oxadiazole (BND), 1,3-bis[5-(4-tert-butylphenyl)-1,3,4-oxadiazolyl)]benzene (BPOB), 1,3,5-tris[5-(4-tert-butylphenyl)-1,3,4-oxadiazolyl]benzene (a compound represented by the formula (3a): TPOB) and 1,3,5-tris[5-(1-naphtyl)-1,3,4-oxadiazolyl]benzene (TNOB)]; a diphenoquinone [for example, a diphenoquinone which may have a substituent (e.g., a $C_{1-10}$alkyl group), such as 3,5,3',5'-tetrakis[tert-butyldiphenoquione]]; 1,2,3,4,5-pentaphenyl-1,3-cyclopentadiene (PPCP); a quinolinolato complex such as tris(8-quinolinolato)aluminum ($Alq_3$), bis(benzoquinolinolato)beryllium complex and tris(10-hydroxybenzo[h]quinolinolato)beryllium complex; and a thiophene such as 1,3,5-tris[5-(dimesitylboryl)-2-thienyl]benzene, 5,5'-bis(dimesitylboryl)-2,2'-bithiophene (a compound represented by the formula (3b): BMB-2T) and 5,5"-bis(dimesitylboryl)-2,2':5',2"-terthiophene (a compound represented by the formula (3c): BMB-3T). Among them, the oxadiazole such as TPOB; the quinolinolato complex such as $Alq_3$; and the thiophene such as 1,3,5-tris[5-(dimesitylboryl)-2-thienyl]benzene, BMB-2T and BMB-3T are preferred. The compound(s) having an electron-transporting function may be used singly or in combination. Incidentally, the above-mentioned $Alq_3$ and 1,3,5-tris[5-(dimesitylboryl)-2-thienyl]

benzene are represented by the following formulae (3d) and (3e), respectively. The compound (3e) was described in Chem. Lett., 2001, 614, which was reported by the inventors of the present invention.

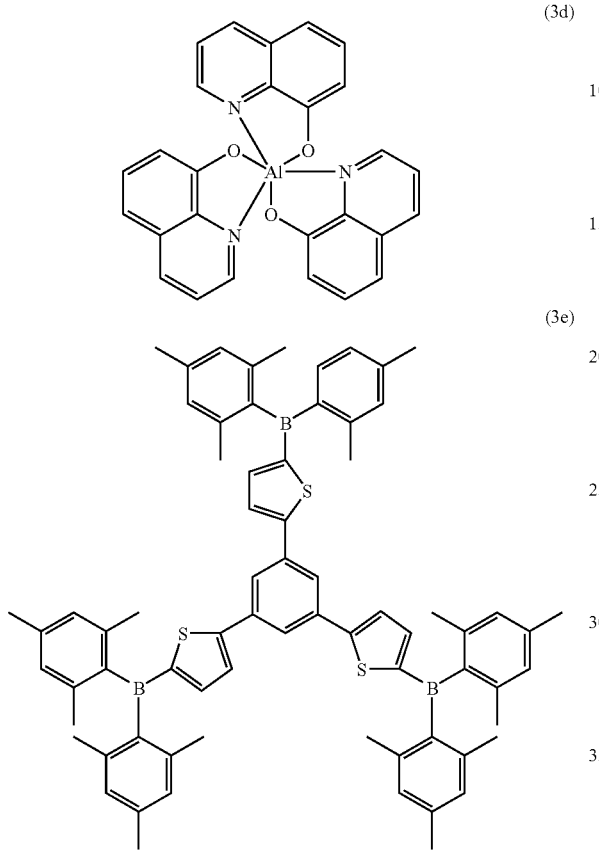

(3d)

(3e)

Exemplified as the organic polymer having an electron-transporting function and/or a hole-transporting function is a vinyl-series polymer having a group which has a hole-transporting function and/or a group which has an electron-transporting function in a main or side chain thereof, for example, a polyphenylenevinylene [for example, a homo- or copolymer of a $C_{6-12}$arylenevinylene, which may have a substituent (e.g., a $C_{1-10}$alkoxy group), such as a polyphenylenevinylene, a poly(2,5-dimethoxyphenylenevinylene) and a polynaphthalenevinylene]; a polyphenylene (in particular, a polyparaphenylene) [for example, a homo- or copolymer of a phenylene, which may have a substituent (e.g., a $C_{1-10}$alkoxy group), such as a polyparaphenylene and a poly-2, 5-dimethoxyparaphenylene]; a polythiophene [a homo- or copolymer of a thiophene, for example, a poly$C_{1-20}$alkylthiophene such as a poly(3-alkylthiophene), a poly$C_{3-20}$cycloalkylthiophene such as a poly(3-cyclohexylthiophene), and a $C_{6-20}$arylthiophene, which may have a substituent (e.g., a $C_{1-10}$alkyl group), such as a poly(3-(4-n-hexylphenyl)thiophene)]; a polyfluorene such as a poly$C_{1-20}$alkylfluorene; a polyvinylcarbazole (e.g., a poly-N-vinylcarbazole (PVK)); a polystyrene (e.g., a poly-4-N,N-diphenylaminostyrene and a poly-4-(5-naphthyl-1,3,4-oxadiazole)styrene); a poly(meth)acrylamide [e.g., a poly (N-(p-diphenylamino)phenylmethacrylamide) and a poly(N, N'-diphenyl-N,N'-bis(3-methylphenyl)-1,1'-biphenyl-4,4'-diaminomethacrylamide) (PTPDMA)]. Further, the organic polymer having an electron-transporting function and/or a hole-transporting function includes a poly$C_{1-4}$alkylphenylsilane such as a polymethylphenylsilane; a polymer having an aromatic amine derivative in a side or main chain thereof; and a copolymer of the monomer constituting the above polymer and a copolymerizable monomer. The organic polymer(s) having an electron-transporting function and/or a hole-transporting function may be used singly or in combination.

As a material constituting the anode buffer layer (hole-injecting layer), there may be mentioned a conventional material for an anode buffer layer, for example, a poly(3,4-ethylenedioxythiophene) (PEDOT) represented by the following formula (5a). PEDOT may be used singly, or may be chemically doped with a polystyrenesulfonate (PSS) represented by the following formula (5b). PEDOT doped with PSS is available from Bayer Ltd. as "BAYTRON P AI 4083" in the state of a water/methanol solution.

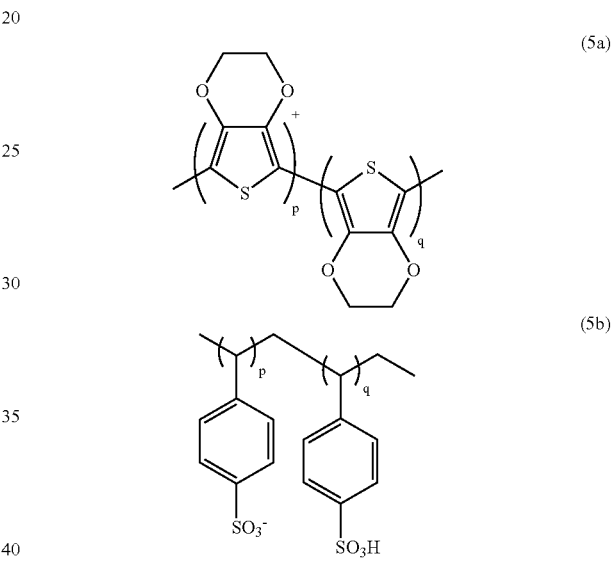

(5a)

(5b)

Wherein p and q denote an integer of not less than 1.

In each of layers constituting the organic EL device (e.g., the hole-transporting layer, the light-emitting layer, the electron-transporting layer, the light-emissive electron-transporting layer), the thickness is not particularly limited, and about 5 nm to 1 μm, preferably about 10 to 800 nm, more preferably about 30 to 500 nm and in particular about 50 to 300 nm.

As the anode of the organic EL device, for example, a transparent conductive membrane or layer (e.g., an indium-tin-oxide (ITO) layer, a tin oxide layer, a zinc oxide layer, and an aluminum layer) is employed. A high conductive metal having a small work function (e.g., magnesium, lithium, aluminum, or silver), calcium or the like is employed as the cathode. In the case where magnesium is employed as the cathode, the magnesium may be coevaporated (or codeposited) with a small amount of silver (e.g., 1 to 10% by weight) for improving the adhesion with a film for an organic EL device. The preferred anode includes a magnesium-silver alloy electrode, an aluminum electrode, a calcium electrode, a lithium/aluminum-laminated electrode, a lithium fluoride/aluminum-laminated electrode, and others.

The layer constituting the organic EL device (e.g., the hole-transporting layer, the light-emitting layer, the electron-transporting layer, the light-emissive electron-transporting layer) can be formed by a conventional method, such as deposition (or evaporation) (e.g., vacuum deposition (or evaporation)), coating or flow casting (e.g., spin coating). Moreover, when a component in each functional layer [such as a hole-transporting compound (a hole-transporting component), a light-emissive compound (a light-emissive component) or an electron-transporting compound (an electron-transporting component)] is poor in film-forming properties, if necessary, a binder resin may be used in combination as far as hole-transporting function, light-emissive property, or electron-transporting function is not inhibited. The binder resin includes various thermoplastic resins [for example, an olefinic resin such as a polyethylene and a polypropylene; a styrenic resin such as a polystyrene and a rubber-modified (or rubber-containing, rubber-reinforced) polystyrene (HIPS); an acrylic resin [e.g., a poly(methyl(meth)acrylate)]; a vinyl alcohol-series polymer such as a polyvinyl alcohol; a vinyl-series resin such as a polyvinyl chloride; a polyamide-series resin such as a 6-nylon; a polyester resin [for example, an alkylene arylate-series resin such as a polyalkylene terephthalate (e.g., a polyethylene terephthalate)]; a fluorine-containing resin; a polycarbonate; a polyacetal; a polyphenylene ether; a polyphenylene sulfide; a polyether sulfone; a polyether ketone; a thermoplastic polyimide; a thermoplastic polyurethane; and a norbornene-series polymer], various thermosetting resins [for example, a phenolic resin, an amino resin (e.g., a urea resin, a melamine resin), a thermosetting acrylic resin, an unsaturated polyester resin, an alkyd resin, a diallyl phthalate resin, an epoxy resin, and a silicone resin]. The binder resin(s) may be used singly or in combination. As the binder resin, a resin having a coating layer-forming capability and soluble in a solvent is usually employed.

In each of the hole-transporting layer, the light-emitting layer, the electron-transporting layer and the light-emissive electron-transporting layer, the ratio of the binder resin may be, for example, about 1 to 70% by weight, preferably about 5 to 50% by weight, and more preferably about 10 to 30% by weight.

The organic EL device of the present invention can be produced by a conventional method, for example, one which comprises forming the transparent electrode on a transparent substrate, forming the layers (e.g., the hole-transporting layer, the light-emitting layer, the electron-transporting layer or light-emissive electron-transporting layer, the anode buffer layer (hole-injecting layer) ) sequentially on the transparent electrode with the use of deposition (or evaporation) or coating of a coating solution (e.g., spin coating), and forming a cathode on the organic layer comprising the above layers to obtain an organic EL device.

Exemplified as the substrate is a transparent substrate (e.g., a glass plate such as a soda glass, a no-alkali glass and a quartz glass, or a sheet or film of a polymer such as a polyester, a polysulfone and a polyethersulfone). For the fabrication of a flexible organic EL device, the polymer film is available.

The organic EL device of the present invention is valuable for utilizing as a variety of display apparatus, for example, a portable information and communication apparatus such as a cellular phone, a data or image processing apparatus (computer system) such as a personal computer, and an image display apparatus such as a television system.

The polymer obtainable from the specific novel vinyl compound (1) is excellent in mold-processability, heat resistance due to its high glass transition temperature, and a hole-transporting function. Therefore, the vinyl compound (1) and the polymer thereof are useful as a material for an organic EL device, and realize great improvement in heat resistance of an organic EL device obtained from the material.

EXAMPLES

The following examples are intended to describe this invention in further detail and should by no means be interpreted as defining the scope of the invention.

Example 1

(1) Synthesis of Vinyl Compound:

4-[bis(4'-t-butylbiphenyl-4-yl)amino]-4'-vinylbiphenyl (VBAB)

(a) Synthesis of bis(4'-t-butylbiphenylyl)-4-bromophenylamine

Aniline (21 mmol) and 4-t-butyl-4'-bromobiphenyl (41 mmol) were dissolved in 120 ml of toluene. To thus obtained solution was added sodium t-butoxide (52 mmol) and a mixture of $Pd(dba)_2$ (0.2 mmol) and DPPF (0.3 mmol) ($Pd(dba)_2$/DPPF), and the resultant mixture was subjected to a reaction at 90° C. for 15 hours in an atmosphere of an inert gas (nitrogen gas). Then, the reaction product was separated by means of a silica gel column chromatography, and was dissolved in 100 ml of chloroform. To thus obtained solution was added 10 mmol of N-bromosuccinic imide (NBS), and the resultant mixture was subjected to a reaction at 25° C. for 1 hour in an atmosphere of an inert gas (nitrogen gas). The reaction product was purified with the use of a silica gel column chromatography to give N,N-bis(4-t-butylbiphenyl)-N-(4-bromophenyl)amine.

(b) Synthesis of 4-(dihydroxyboro)styrene

In 50 ml of tetrahydrofuran, 4-bromostyrene (16 mmol) was allowed to react with metal magnesium (16 mmol) at 25° C. for 1 hour in an atmosphere of an inert gas (nitrogen gas) to prepare a Grignard reagent represented by the formula (1e). To the reaction mixture was added 29 mmol of orthoboric acid, and thus obtained mixture was subjected to a reaction at 0° C. for 1 hour in an atmosphere of an inert gas (nitrogen gas). Then, water (1 mol) was added to the reaction mixture, and stirred at 80° C for 24 hours to give p-(dihydroxyboro)styrene represented by the formula (1f).

(c) Synthesis of 4-[bis(4'-t-butylbiphenyl-4-yl) amino]-4'-vinylbiphenyl (VBAB)

N,N-bis(4-t-butylbiphenyl)-N-(4-bromophenyl)amine (7.6 mmol) obtained from the above step (a) and p-(dihydroxyboro)styrene (7.6 mmol) obtained from the above step (b) were dissolved in 100 ml of toluene, and allowed to react in the presence of palladium tetrakis(triphenylphosphine) (0.15 mmol) and sodium carbonate (100 mmol) at 80° C. for 24 hours in an atmosphere of an inert gas (nitrogen gas) to give VBAB.

Incidentally, the obtained VBAB was subjected to various spectral measurements, and elemental analysis. The spectral measurements were carried out according to the following manner.

$^1$H-NMR spectrum and $^{13}$C-NMR spectrum were measured with the use of tetramethylsilane (TMS) as an internal standard in deuterochloroform (CDCl$_3$) or deuterodimethylsulfoxide (d$_6$-DMSO) by means of a Varian Unity-plus 300 NMR spectrometer. Mass spectrum was measured by means of a GCMS-QP5000 spectrometer (manufactured by Shimadzu Corporation). UV/visible spectrum and fluorescence spectrum were determined by dissolving the obtained sample in chloroform at a proportion of 1.5×10$^{-5}$ mol/L and measuring the UV/visible and fluorescence spectra of the resultant solution of the sample with the use of a U-2010 spectrometer (manufactured by Hitachi, Ltd.) and a F-4500 fluorescence spectrometer (manufactured by Hitachi, Ltd.), respectively.

NMR (CDCl$_3$) (ppm): 1.36 (s, 18H), 5.25 (d, 1H), 5.78 (d, 1H), 6.71 (dd, 1H), 7.28 (dd, 2H), 7.44 (d, 4H), 7.47 (d, 4H), 7.51 (d, 4H)

Mass spectrum (m/e): 611.5

Peak wavelength of the absorption spectrum (uv): λmax 352 nm (extinction coefficient εmax 60250)

Peak wavelength of the fluorescence spectrum: Fmax 436 nm

Elemental analysis (C H N ):
Calculated value: C=90.30%; H=7.41%; N=2.29%
Found value: C=90.29%; H=7.43%; N=2.33%

(2) Synthesis of polyVBAB (PVBAB)

A benzene solution containing 2,2'-azobisisobutyronitrile (AIBN) as a radical initiator and the vinyl compound VBAB obtained from the above step (1) in a concentration of 0.01 mol/ml and 1.0 mol/ml, respectively was subjected to a polymerization with heating and shaking at 65° C. for 36 hours under deaeration. Then, the polymerization product was purified by reprecipitation three times with benzene and methanol to give pale yellow and powdered PVBAB [(yield (in terms of VBAB): 40%].

(a) Identification of PVBAB

The obtained PVBAB was subjected to various spectral measurements, and elemental analysis in the same manner as in the above-mentioned VBAB.

NMR (CDCl$_3$) (ppm): 1.22–1.42 (m, 21H), 7.58–8.91 (m, 24H)

Peak wavelength of the absorption spectrum (uv) : λmax 346 nm (extinction coefficient εmax 55000)

Peak wavelength of the fluorescence spectrum: Fmax 408 nm (b) Molecular Weight

According to GPC, the number-average molecular weight (Mn) and weight-average molecular weight (Mw) in terms of polystyrene were determined as 21,000 and 39,000, respectively.

(c) Solubility

The solubility of PVBAB was evaluated in the condition of a temperature of 25° C. PVBAB was soluble easily in an organic solvent of benzene, THF, toluene and chloroform.

(d) Measurement of Electronic Absorption Spectrum

Figure 5:
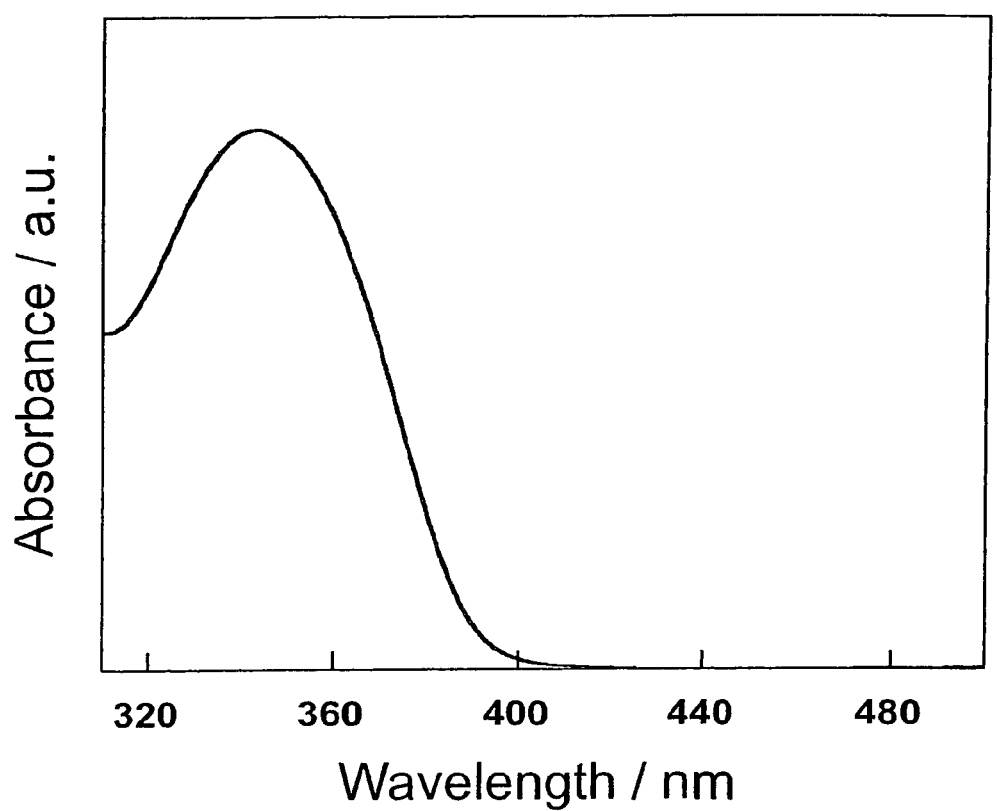
FIG. 5 is an electronic absorption spectrum of the PVBAB thin layer obtained in Example 1.

A thin layer 70 nm (700 Å) thick was formed on a substrate by using a benzene solution containing PVABA (1×10$^{-5}$ mol/ml) by spin coating method. By using the thin layer, the electronic absorption spectrum was measured. The result is shown in FIG. 5. As apparent from FIG. 5, the PVBAB thin layer was uniform and transparent. Moreover, Optical Band Gap was 3.2 eV, and the energy level of LUMO was -2.4 eV.

(e) Measurement of Glass Transition Temperature (Tg)

Figure 6:
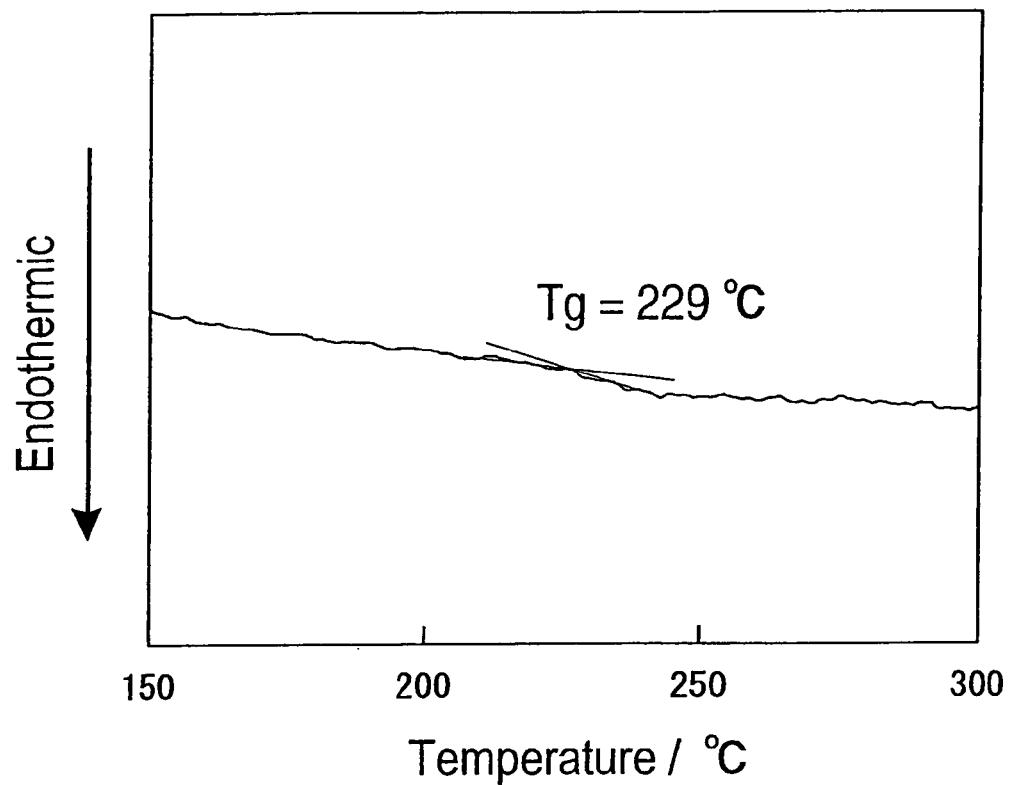
FIG. 6 is a DSC curve of the PVBAB obtained in Example 1.

The glass transition temperature (Tg) of PVBAB was determined by carrying out a differential scanning calorimetry at a programming rate of 5° C./minute. The DSC curve of PVBAB is shown in FIG. 6. As apparent from the DSC curve of FIG. 6, Tg of PVBAB was 229° C., and PVABA had very high glass transition temperature over 200° C.

(f) Cyclic Voltammogram

Figure 7:
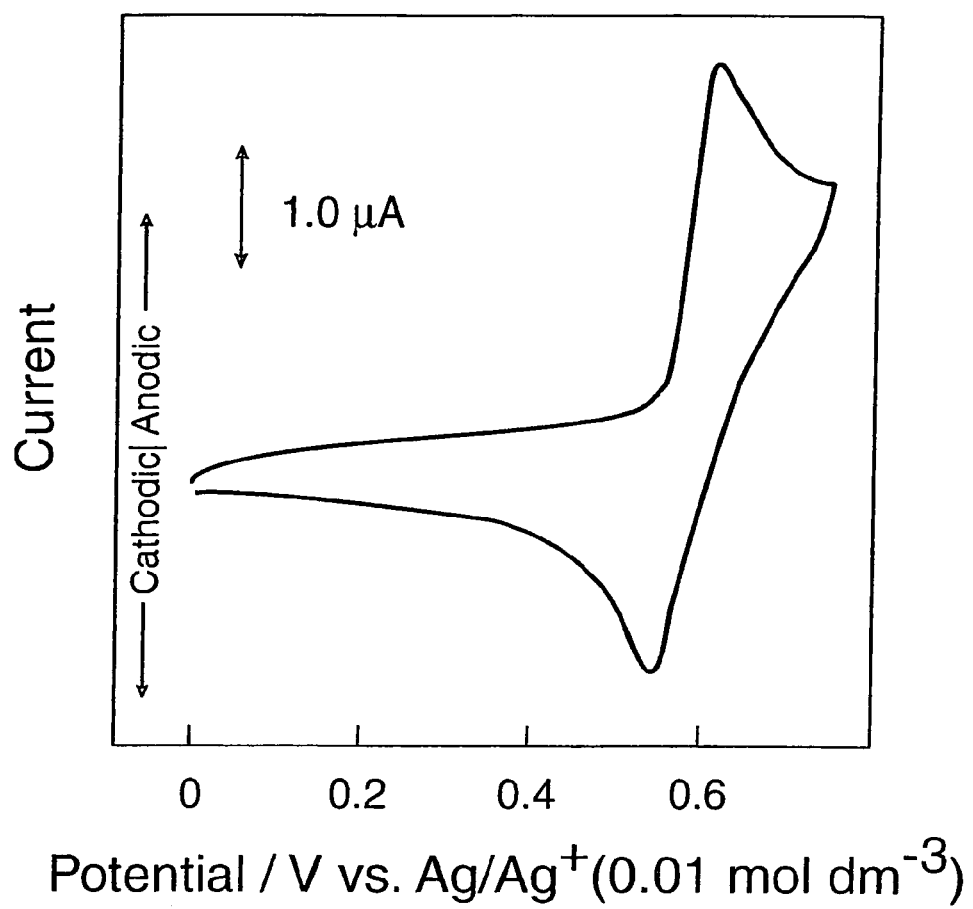
FIG. 7 is a cyclic voltammogram of the PVBAB obtained in Example 1.

The cyclic voltammogram was determined by using a dichloromethane solution containing PVBAB (1×10$^{-3}$ mol/ml) and Bu$_4$ClO$_4$ as a supporting electrolyte (1×10$^{-4}$ mol/ml) at a sweep rate of 100 mVs$^{-1}$. The result is shown in FIG. 7. Even when potential-sweep was repeated, neither new oxidation wave nor new reduction wave was recognized. It was found that the potential difference between a peak of oxidation wave and that of reduction wave ($E_{pa} - E_{pc}$) was 0.062 V, $i_{pc}/i_{pa}$ in Nicholson's formula was 1, the anodic oxidation step of PVBAB was electrically reversible, and radical cations are present stably. The oxidation potential ($E_{1/2}$) of PVBAB relative to an Ag/Ag$^+$ reference electrode was 0.58 vs. Ag/Ag$^+$ (0.01 mol/ml). Thus, PVBAB had low oxidation potential, and it is appreciated that PVBAB is suitable for a hole-transporting layer of an organic EL device.

(3) Producing of an Organic EL Device Using PVBAB as a Hole-Transporting Layer

Figure 4:
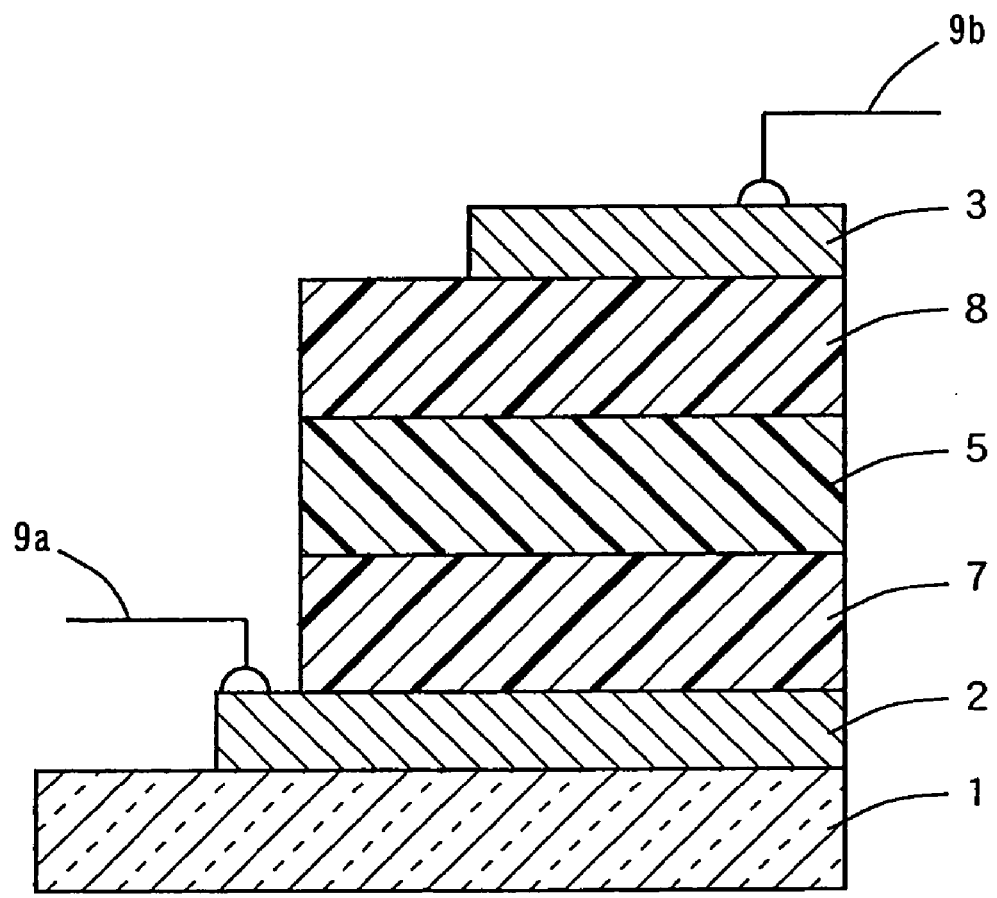
FIG. 4 is a schematic sectional view showing a yet another embodiment of the organic EL device of the present invention.

An organic EL device shown in FIG. 4 was made according to the following procedure. That is, on an ITO substrate, in which an ITO (indium-tin-oxide) electrode 2 was formed on a glass substrate 1, was coated a material in which a polystyrenesulfonate (PSS) represented by the formula (5b) was chemically doped with a poly(3,4-ethylenedioxythiophene) (PEDOT) represented by the formula (5a) [BAYTRON P AI 4083, manufactured by Bayer Ltd.], by spin coating to form an anode buffer layer (hole-injecting layer) 7 having a thickness of 100 nm (1000 Å) thick.

Then, A tetrahydrofuran solution containing PVBAB was coated on the anode buffer layer by spin coating to form a hole-transporting layer 70 nm thick. Further, tris(8-quinolinolato)aluminum (Alq$_3$) represented by the formula (3d) was vacuum-deposited (or vacuum-evaporated) on the hole-transporting layer to form a light-emissive electron-transporting layer 30 nm thick. A back electrode (area: 4 mm$^2$) comprising an alloy of magnesium and silver (volume ratio: magnesium/silver=10/1) (MgAg electrode) was deposited (or evaporated) on the light-emissive electron-transporting layer to give an organic EL device.

(4) Evaluation of Organic EL Device (a) Emitting Property

Figure 8:
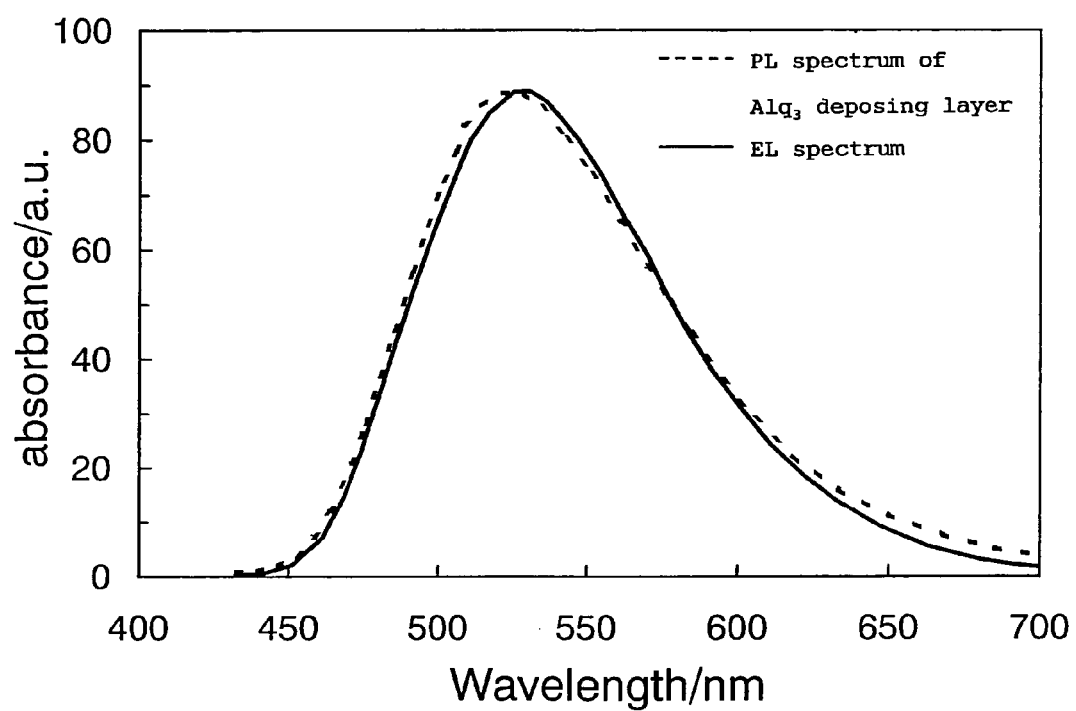
FIG. 8 is an EL spectrum of the organic EL device and a fluorescence spectrum of the Alq$_3$ depositing layer obtained in Example 1.

In the formed organic EL device, a voltage of not less than 3 V was applied between the ITO electrode and the MgAg electrode, and green emission was observed. An EL spectrum of the organic EL device is shown in FIG. 8 together with a fluorescence spectrum of an Alq$_3$ depositing layer. As apparent from FIG. 8, the EL spectrum of the organic EL device well agrees with the fluorescence spectrum of the Alq$_3$ depositing layer, and therefore it is considered that an emission species of the organic EL device is Alq$_3$.

Incidentally, regarding the above-mentioned organic EL device, the maximum luminance was 11,500 cd·m$^{-2}$ at 12 V. When the luminance was 100 cd·m$^{-2}$, the luminous efficiency was 2.01 m·W$^{-1}$, quantum efficiency (quantum yield) was 1.0%, and green emission having high luminance and high efficiency was observed.

(b) Heat Resistance

Figure 9:
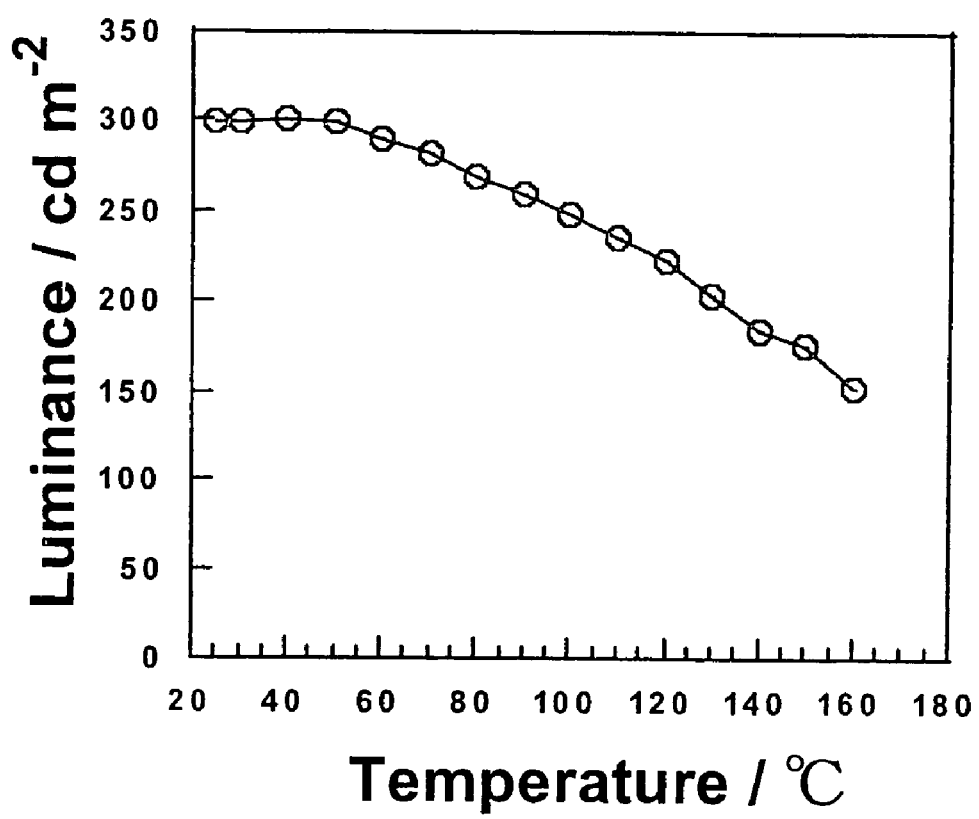
FIG. 9 is a graph showing change of a luminance (emitting luminance) depending on temperature change in the organic EL device obtained in Example 1.

The heat resistance was evaluated by driving the organic EL device at a constant current with varying the temperature under reduced pressure of 0.1 Torr, and determining luminance of the device at each temperature. A relationship of a temperature and a luminance is shown in FIG. 9. In FIG. 9, the luminance decays in accordance with rise in temperature.

The decay is effected by deterioration in fluorescence quantum efficiency of the light-emitting material or deterioration in a balance of a hole relative to an electron, and is not effected by degradation of the used organic material. This was confirmed by the following reason: in the case where once heated device was cooled to room temperature, the luminance was recovered to the same degree as that before heating. Thus, the organic EL device of the Example can drive stably even in such a high temperature range as approximately 150° C.

Example 2

An organic EL device was produced in the same manner as in Example 1 except that an anode buffer layer was formed with PEDOT and the thickness of the Alq$_3$ layer was 80 nm.

Figure 10:
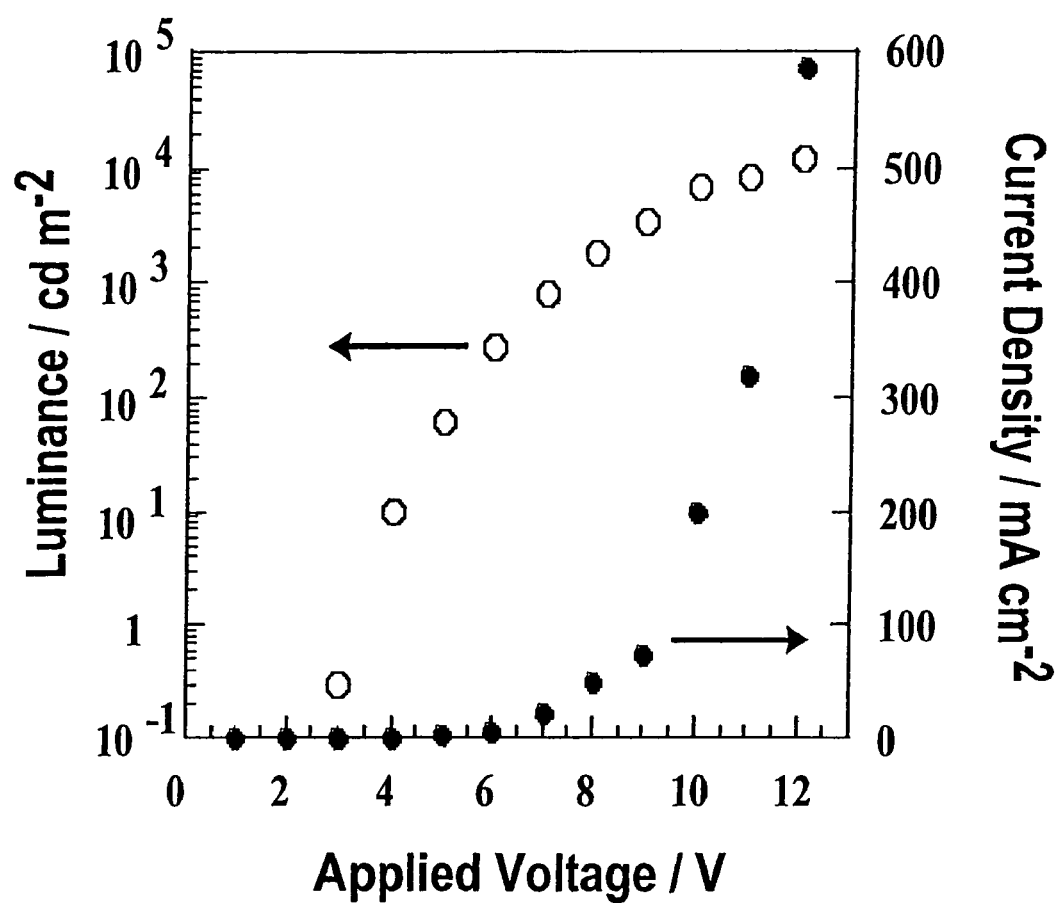
FIG. 10 is a graph showing a relationship between an applied voltage, and a luminance (emitting luminance) and a current density in the organic EL device obtained in Example 2.

The obtained organic EL device showed green emission due to an emission of Alq$_3$ similar to Example 1, by applying 3.0 V of a voltage. A relationship between a voltage applied on the device, and a luminance and a current density is shown in FIG. 10. In the obtained device, the maximum luminance was 11,500 cd·m$^{-2}$ (at 12 V), the luminous efficiency was 2.01 m·W$^{-1}$ when the luminance was 300 cd·m$^{-2}$, and the device was shown excellent hole-transporting ability.

What is claimed is:

1. An organic electroluminescent device, which comprises an organic layer between a pair of electrodes, and the organic layer comprises at least one layer containing a vinyl polymer comprising a unit represented by the following formula (2):

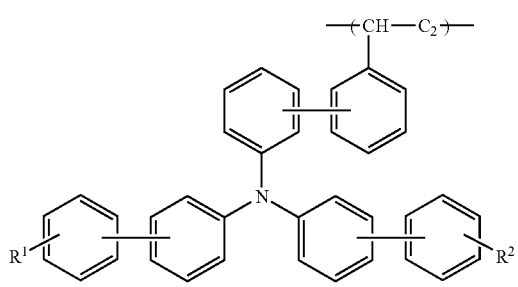

(2)

wherein R$^1$ and R$^2$ are the same or different, each representing a hydrogen atom, a halogen atom, an alkyl group or an alkoxy group;

wherein the organic layer comprises (a) a hole-transporting layer containing the vinyl polymer, a light-emitting layer and an electron-transporting layer, or (b) a hole-transporting layer containing the vinyl polymer and a light-emissive electron-transporting layer, and an anode buffer layer is interposed between the hole-transporting layer and an anode of the electrodes, and wherein the anode buffer layer comprises a poly(3,4-ethylenedioxythiophene) chemically doped with a polystyrene.

2. A vinyl polymer comprising a unit represented by the following formula (2):

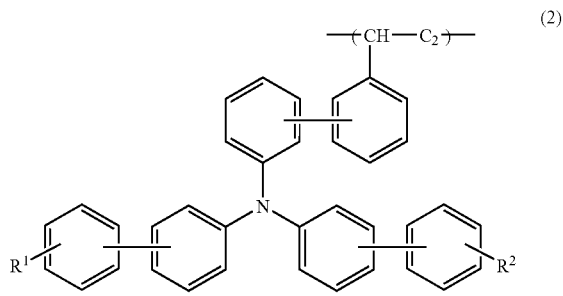

(2)

wherein R$^1$ and R$^2$ are the same or different, each representing a hydrogen atom, a halogen atom or an alkoxy group.

3. The vinyl polymer according to claim 2, wherein the vinyl polymer is a homopolymer of a vinyl compound represented by the following formula (1):

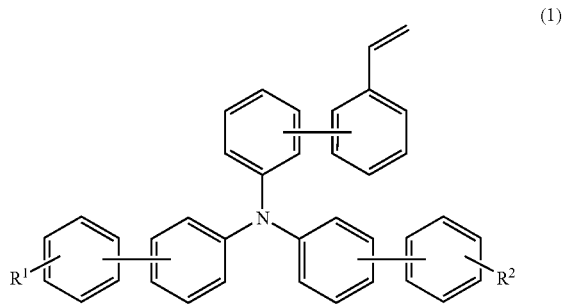

(1)

wherein R$^1$ and R$^2$ are the same or different from each other, and each represents a hydrogen atom, a halogen atom or an alkoxy group; or the vinyl polymer is a copolymer of the vinyl compound and a copolymerizable monomer.

4. The vinyl polymer according to claim 2, wherein the glass transition temperature of the vinyl polymer is 200 to 250° C.

5. The vinyl polymer according to claim 2, wherein the number-average molecular weight of the vinyl polymer is 5,000 to 500,000.

* * * * *